(12) United States Patent
Richter et al.

(10) Patent No.: US 7,314,711 B2
(45) Date of Patent: Jan. 1, 2008

(54) ASSAYS EMPLOYING ELECTROCHEMILUMINESCENT LABELS AND ELECTROCHEMILUMINESCENCE QUENCHERS

(75) Inventors: Mark M. Richter, Springfield, MO (US); Michael J. Powell, Danville, CA (US); Christopher M. Belisle, Concord, CA (US)

(73) Assignee: BioVeris Corporation, Gaithersburg, MD (US)

( * ) Notice: Subject to any disclaimer, the term of this patent is extended or adjusted under 35 U.S.C. 154(b) by 0 days.

(21) Appl. No.: 09/074,472

(22) Filed: May 7, 1998
(Under 37 CFR 1.47)

(65) Prior Publication Data

US 2001/0023063 A1    Sep. 20, 2001

Related U.S. Application Data

(60) Provisional application No. 60/047,605, filed on May 23, 1997.

(51) Int. Cl.
*C12Q 1/68* (2006.01)
*C12P 19/34* (2006.01)
*C07H 21/02* (2006.01)

(52) U.S. Cl. .................. 435/6; 435/91.2; 536/23.1; 536/24.3

(58) Field of Classification Search .............. 435/6, 435/7, 91.1, 91.2, 252.8, 320.1, 183; 536/22.1, 536/23.1, 24.3–24.33; 702/19, 22
See application file for complete search history.

(56) References Cited

U.S. PATENT DOCUMENTS

| | | | |
|---|---|---|---|
| 3,996,345 A | 12/1976 | Ullman et al. ................ 424/12 |
| 4,161,515 A | 7/1979 | Ullman ........................ 424/8 |
| 4,208,479 A | 6/1980 | Zuk et al. .................... 435/7 |
| 4,233,401 A | 11/1980 | Yoshida et al. ............... 435/7 |
| 4,256,834 A | 3/1981 | Zuk et al. .................... 435/7 |
| 4,261,968 A | 4/1981 | Ullman et al. ................ 424/8 |
| 4,293,310 A * | 10/1981 | Weber ...................... 23/230 B |
| 4,444,887 A | 4/1984 | Hoffmann ................... 435/240 |
| 4,472,500 A | 9/1984 | Milstein et al. ............. 435/68 |
| 4,491,632 A | 1/1985 | Wands et al. ............... 435/240 |
| 4,743,535 A * | 5/1988 | Carrico |
| 5,068,088 A | 11/1991 | Hall et al. .................. 422/52 |
| 5,147,806 A | 9/1992 | Kamin et al. ............... 436/149 |
| 5,221,605 A | 6/1993 | Bard et al. .................. 435/4 |
| 5,332,662 A | 7/1994 | Ullman ....................... 435/28 |
| 5,763,158 A * | 6/1998 | Bohannon ................... 435/4 |
| 5,798,276 A * | 8/1998 | Haugland et al. .......... 436/546 |
| 6,132,955 A * | 10/2000 | Talley et al. ............... 435/4 |

FOREIGN PATENT DOCUMENTS

EP   0745690 A2   12/1996

| | | | |
|---|---|---|---|
| WO | WO 90/05302 | 5/1990 |
| WO | WO 92/14139 | 8/1992 |
| WO | WO 93/12256 | * 12/1992 | .................. 435/6 |

OTHER PUBLICATIONS

Sigma Catalog (pp. 151, 789 and 1820), 1995.*
Stratagene Catalog (p. 39), 1988.*
Chmura et al., "Assay of antioxidants by the quenching of the anthracene-sensitized electrochemiluminescence", Journal of Biolumin chemilumin, vol. 9, pp. 1-6, 1994.*
Papalambros et al., "Benzylidene fluorene ozonolysis under chemiluminescence mimetic conditions in homogeneous and micellar media: rate constants of fluorenone quenching by the leaving moiety", Journal of Photochemistry, vol. 39, pp. 85-96, Jan. 2, 1987.*
IGENE Catalog, 1996.*
Rajagopal et al (J. Photochem. Photobiol. A: Chem (1992) 69:83-89).*
Vera et al. (J. Photochm. Photobiol. A: Chem (1993) 76:13-19).*
Kuzmin et al (J. Photochem. Photobiol. A: Chem (1995) 87:43-54).*
Kricka, 1992, ed., *Nonisotopic DNA Probe Techniques* (Academic Press, New York).
Leland et al., 1990, "Electrogenerated Chemiluminescence: An Oxidation-Reduction Type ECL Reaction Sequence using Tripropyl Amine," *J. Electrochem. Soc.*, vol. 137, No. 10, pp. 3127-3131.
Maliwal et al., 1995, "Fluorescence Energy Transfer in One Dimension: Frequency-Domain Fluorescence Study of DNA-Fluorophore Complexes," *Biopolymers*, vol. 35, pp. 245-255.
Masseyeff et al., 1993, eds., *Methods of Immunological Analysis* (Weinheim: VCH Verlags gesellschaft mbH).
Tyagi et al., 1996, "Molecular Beacons: Probes that Fluoresce upon Hybridization," *Nature Biotechnology*, vol. 14, pp. 303-308, Mar. 1996.
Weir et al., 1996, eds., Handbook of Experimental Immunology, 5th Edition (Blackwell Science).
Wild, 1994, ed., *The Immunoassay Handbook* (Stockton Press, NY).
Wittwer et al., 1997, "Continuous Fluorescence Monitoring of Rapid cycle DNA Amplification," *Biotechniques*, vol. 22, pp. 130-138, Jan. 1997.
Yost, 1993, "Electrochemiluminescence (ECL)—A New Detection System for Immunoassays and DNA Probe Assays," in *Scientific Bavaria '92, 4th International Symposium, Progress in Laboratory Diagnostics*, eds. W. Holzel and S. Klose, published by Urban & Vogel, Munchen, pp. 82-90.

(Continued)

*Primary Examiner*—Jeffrey Fredman
(74) *Attorney, Agent, or Firm*—Foley & Lardner LLP

(57) ABSTRACT

This invention pertains to the general field of chemical and biological assays which employ electrochemiluminscence (ECL), also referred to as electrogenerated chemiluminescence. More particularly, the present invention pertains to certain classes of chemical moieties which strongly quench ECL, and the use of these ECL quenchers in combination with ECL labels, for example, in ECL assay methods which employ an ECL quencher and an ECL label. One class of such quenching moieties are those which comprise at least one benzene moiety. Sub-classes of such quenching moieties are those which comprise at least one phenol moiety, quinone moiety, benzene carboxylic acid, and/or benzene carboxylate moiety.

7 Claims, 6 Drawing Sheets

OTHER PUBLICATIONS

Abruna et al., 1985, "Electrochemiluminescence of Osmium Complexes. Spectral, Electrochemical, and Mechanistic Studies," *J. Electrochem. Soc., Electrochem. Sci. and Tech.*, vol. 132, No. 4, pp. 842-849.

Blackburn et al., 1991, "Electrochemiluminescence Detection for Development of Immunoassays and DNA Probe Assays for Clinical Diagnostics," *Clin. Chem.*, vol. 37, No. 9, pp. 1534-1539.

Chmura et al., 1994, "Assay of Antioxidants by the Quenching of the Anthracene-Sensitized Electrochemiluminescence," *J. Biolumin. Chemilumin.*, vol. 9, pp. 1-6.

Coligan et al.,1991, eds., *Current Protocols in Immunology* (Published by Wiley & Co.).

Dallakyan et al., 1978, "A Method of Determining Small Concentrations of Phenols and Substances Containing Sulfhydryl Groups," Gidrobiologicheskii Zhurnal, vol. 14, No. 5, pp. 105-109. (English abstract provided).

Greenway et al., 1995, "Electrogenerated Chemiluminescent Determination of Codeine and Related Alkaloids and Pharmaceuticals With Tris(2,2'-bipyridine)ruthenium(II)," *Analyst*, vol. 120, pp. 2549-2552.

Gudibande et al., 1992, "Rapid, Non-Separation Electrochemiluminescent DNA Hybridization Assays for PCR Products, Using 3'-Labeled Oligonucleotide Probes," *Mol. Cell. Probes*, vol. 6, No. 6, pp. 495-503.

Harlow & Lane, 1988, *Antibodies: A Laboratory Manual* (Cold Spring Harbor Laboratory).

Heid et al., 1996, "Real Time Quantitative PCR," *Genome Research*, vol. 6, No. 10, Oct. 1996, pp. 986-994.

Hill et al., 1988, "Electrochemiluminescence as a Detection Technique for Reversed-Phase High-Performance Liquid Chromatography. IV. Detection of Fluorescent Derivatives," *J. Chromatography*, vol. 441, pp. 394-399.

Kenten et al., 1991, "Rapid Electrochemiluminescence Assays of Polymerase Chain Reaction Products," *Clin. Chem.*, vol. 37, No. 9, pp. 1626-1632.

Knight et al., 1994, "Occurrence, Mechanisms and Analytical Applications of Electrogenerated Chemiluminscence," *Analyst*, vol. 119, pp. 879-890.

Kricka, 1991, "Chemiluminescent and Bioluminscent Techniques," *Clin. Chem.*, vol. 37, No. 9, pp. 1472-1481.

DiCesare, J. et al., "A High-Sensitivity Electrochemiluminescence-Based Detection System for Automated PCR Product Quantitation," *Bio Techniques*, 15:152-57 (1993).

Yu, H. et al., "Enhancing Immunoelectrochemiluminescence (IECL) for Sensitive Bacterial Detection," *J. Immunol. Methods*, 192:63-71 (1996).

Search Report dated Apr. 5, 2004, from EP Application No. 03015594.9-2404.

* cited by examiner

ASSAYS EMPLOYING ELECTROCHEMILUMINESCENT LABELS AND ELECTROCHEMILUMINESCENCE QUENCHERS

RELATED APPLICATIONS

This application claims priority under 35 U.S.C. § 119(e) to U.S. Provisional Patent Application No. 60/047,605 filed May 23, 1997, the disclosure of which is incorporated herein by reference.

TECHNICAL FIELD

This invention pertains to the general field of chemical and biological assays which employ electrochemiluminescence (ECL), also referred to as electrogenerated chemiluminescence. More particularly, the present invention pertains to certain classes of chemical moieties which strongly quench ECL, and the use of these ECL quenchers in combination with ECL labels, for example, in ECL assay methods which employ an ECL quencher and an ECL label. One class of such quenching moieties are those which comprise at least one benzene moiety. Sub-classes of such quenching moieties are those which comprise at least one phenol moiety, quinone moiety, benzene carboxylic acid, and/or benzene carboxylate moiety.

BACKGROUND

Throughout this application, various publications, patents, and published patent applications are referred to by an identifying citation; full citations for these documents may be found at the end of the specification immediately preceding the claims. The disclosures of the publications, patents, and published patent specifications referenced in this application are hereby incorporated by reference into the present disclosure to more fully describe the state of the art to which this invention pertains.

Luminescence is the term commonly used to refer to the emission of light from a substance for any reason other than a rise in its temperature. In general, atoms or molecules emit photons of electromagnetic energy (e.g., light) when they move from an "excited state" to a lower energy state (usually the ground state); this process is often referred to as "radiative decay." There are many causes of excitation. If exciting cause is a photon, the luminescence process is referred to as "photoluminescence." If the exciting cause is an electron, the luminescence process is referred to as "electroluminescence." More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence." Luminescence produced by a living organism is usually referred to as "bioluminescence." If photoluminescence is the result of a spin-allowed transition (e.g., a single-singlet transition, triplet-triplet transition), the photoluminescence process is usually referred to as "fluorescence." Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence." Typically, phosphorescence emissions persist long after the exciting cause is removed as a result of long-lived excited states which may relax only through such spin-forbidden transitions.

Electrochemiluminescence ("ECL"), also referred to as electrogenerated chemiluminescence, generally pertains to the emission of photons of electromagnetic radiation (e.g., light) from an electronically excited chemical species which has been generated electrochemically. In a simple example, species A, in the ground state, is first electrochemically reduced to form a reduced species $A^-$ that may then diffuse from the electrode surface. Similarly, a species A is electrochemically oxidized to form an oxidized species $A^+$. The reduced species $A^-$ and the oxidized species $A^+$ then diffuse together and react to form an electronically excited species, $A^*$, and a ground state species, A. The electronically excited species, $A^*$, then relaxes to the ground state by emitting a photon.

$A + e^- \rightarrow A^-$
$A - e^- \rightarrow A^+$
$A^- + A^+ \rightarrow A^* + A$
$A^* \rightarrow A + h_\nu$ In common similar examples, a coreactant, CR, reacts with either an electrochemically generated reduced or oxidizes species, A+ or A−, to form an electronically excited species $A^*$, when then relaxes to the ground state by emitting a photon.

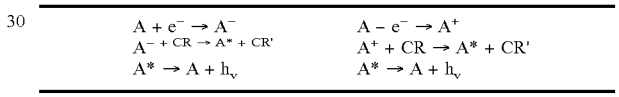

ECL was first observed in the late 1920's and was investigated in detail during the late 1960's and 1970's. A number of literature reviews pertaining to the nature ECL (e.g., the emitting state, the emission mechanism, the emission efficiency) have been published. See, for example, Knight et al., 1994 and references cited therein.

ECL of polyaromatic hydrocarbons in both aqueous and non-aqueous media has been widely studied. Examples of such compounds include naphthalene, anthracene, phenanthrene, pyrene, chrysene, perylene, coronene, and rubrene.

A typical example is the ECL of 9,10-diphenylanthracene ("DPA"). A double potential step is applied to a platinum electrode, producing anodic oxidation products (i.e., the radical cation, $DPA^{*+}$) at the positive potential and cathodic reduction products (i.e., the radical anion, $DPA^{*-}$) at the negative potential. The products undergo electron transfer to yield DPA and electronically excited (singlet) state $^1DPA^*$, which emits a photon via chemiluminescence (in this case, fluorescence). In this example, the emitting state is formed directly upon electron transfer (so called "S-route").

$DPA - e^- \rightarrow DPA^{*+}$ (electro-oxidation)
$DPA + e^- \rightarrow DPA^{*-}$ (electro-reduction)
$DPA^{*+} + DPA^{*-} \rightarrow DPA + {}^1DPA^*$ (electron transfer)
$^1DPA^* \rightarrow DPA^{*-} + h_\nu$ (chemiluminescence)

ECL may also be generated using polyaromatic hydrocarbons in combination with other chemical species which may act as suitable donor or acceptor molecules in the electron transfer step. For example, another common ECL system involves DPA and the donor species, N,N',N'',N'''-tetramethyl-para-phenylenediamine ("TMPD"). In this case, the emitting state is formed in a second (inefficient) triplet-triplet annihilation step from the product of the first electron transfer step (so-called "T-route").

TMPD−e⁻→TMPD*+ (electro-oxidation)
DPA+e⁻→DPA*− (electro-reduction)
TMPD*+ +DPA*− →TMPD+³DPA* (electron transfer 1)
³DPA*+³DPA*→DPA+¹DPA* (electron transfer2)
¹DPA*→DPA*−+h$_v$ (chemiluminescence)

ECL of inorganic and/or organometallic compounds has also been widely studied. An important class of such compounds are the 2,2'-bipyridine ("bpy") complexes of ruthenium and osmium, such as $Ru(bpy)_3^{2+}$ and $Os(bpy)_3^{2+}$. Other examples of such compounds include tricarbonyl (chloro)(1,10-phenanthroline) rhenium(I), square planer platinum(II) complexes, $Cr(bpy)_3^{2+}$, multinuclear complexes such as $Pt_2(diphosphonate)_4^{4-}$, and clusters such as $Mo_6Cl_{12}^{2-}$. See, for example, Knight et al., 1994.

Most investigations of inorganic and/or organometallic compounds have centered on $Ru(bpy)_3^{2+}$ and related compounds primarily due to their intrinsic, and somewhat exceptional, properties, including the ability to emit luminescence at room temperature in aqueous solution, the ability to undergo reversible one-electron transfer reactions at easily attainable potentials, leading to sufficiently stable reduced or oxidized species, insensitivity to the presence of oxygen, and an annihilation efficiency of nearly 100% under certain conditions. For example, if a solution of $Ru(bpy)_3^{2+}$ is subjected to a cyclic double-step potential alternating between the oxidation and reduction potential of the complex, an orange emission is observed (at ~620 nm).

$Ru(bpy)_3^{2+}-e^-\rightarrow Ru(bpy)_3^{3+}$ (electro-oxidation)
$Ru(bpy)_3^{2+}+e^-\rightarrow Ru(bpy)_3^+$ (electro-reduction)
$Ru(bpy)_3^+ +Ru(bpy)_3^{3+}\rightarrow Ru(bpy)_3^{2+}+Ru(bpy)_3^{2+*}$ (electron transfer)
$Ru(bpy)_3^{2+*}\rightarrow Ru(bpy)_3^{2+}+h_v$ (chemiluminescence)

ECL may also be generated using $Ru(bpy)_3^{2+}$ in combination with strong oxidizing or reducing species in solution; in this way, only half of the double-step oxidation-reduction cycle need be applied. For example, coreactants peroxodisulfate (i e., $S_2O_8^{2-}$, persulfate) and oxalate (i.e., $C_2O_4^{2-}$) are irreversibly reduced or oxidized, respectively, to form oxidizing $SO_4^{*-}$ or reducing $CO_2^{*-}$ ions. For example, $Ru(bpy)_3^{2+}+e^-\rightarrow Ru(bpy)_3^+$ (electro-reduction)
$S_2O_8^{2-}+e^-\rightarrow SO_4^{2-}+SO_4^{*-}$ (electro-reduction)
$SO_4^{*-}+Ru(bpy)_3^+\rightarrow SO_4^{2-}+Ru(bpy)_3^{2+*}$ (electron transfer)
$SO_4^{*-}+Ru(bpy)_3^{2+}\rightarrow SO_4^{2-}+Ru(bpy)_3^{3+}$ (electron transfer)
$Ru(bpy)_3^+ +Ru(bpy)_3^{3+}\rightarrow Ru(bpy)_3^{2+}+Ru(bpy)_3^{2+*}$ (electron transfer)
$Ru(bpy)_3^{2+*}\rightarrow Ru(bpy)_3^{2+}+h_v$ (chemiluminescence)

In a similar manner, ECL may also be generated using $Ru(bpy)_3^{2+}$ in combination with coreactants such as amines, or compounds containing amine groups, which act as reducing agents. In general, emission from the $Ru(bpy)_3^{2+}$ ECL reaction with amines increases in the order, primary <secondary<tertiary. Aliphatic or alicyclic amines are generally more efficient than aromatic amines. An example of a commonly used amine is tri-n-propylamine (i.e., $N(CH_2CH_2CH_3)_3$, "TPAH"). See, for example, Leland et al., 1990. It is commonly believed that a proton is lost from an α-carbon of one propyl group upon electro-oxidation and subsequent reaction, to yield TPA* (i.e., $(CH_3CH_2CH_2)_2N(CHCH_2CH_3)^*$). The ECL sequence is summarized by the reactions below.

$Ru(bpy)_3^{2+}-e^-\rightarrow Ru(bpy)_3^{3+}$ (electro-oxidation)
TPAH−e⁻→[TPAH]⁺→TPA*+H⁺ (electro-oxidation and reaction)
$Ru(bpy)_3^{3+}+TPA^* \rightarrow Ru(bpy)_3^{2+*}+$products (electron transfer)
$Ru(bpy)_3^{2+*}\rightarrow Ru(bpy)_3^{2+}+h_v$ (chemiluminescence)

In this way, ECL of $Ru(bpy)_3^{2+}$ has been employed in the determination of a wide range of coreactants. For example, $Ru(bpy)_3^{2+}$ ECL has been effectively used to determine oxalate and persulfate to levels as low as $10^{-13}$ moles/liter. Similarly, $Ru(bpy)_3^{2+}$ ECL has been employed in the determination of aliphatic amines, alicyclic amines (such as sparteine, nicotine, and atropine), drugs such as erythromycin (which has a trialkylamine group), amino acids (such as valine and proline), and proteins. This in turn has led to the implementation of $Ru(bpy)_3^{2+}$, as well as other ruthenium and osmium chelates, as sensitive ECL labels for chemical and biochemical assays.

Chemical and biological assays generally involve contacting the analyte of interest with a pre-determined non-limiting amount of one or more assay reagents, measuring one or more properties of a resulting product (the detection product(s)), and correlating the measured value with the amount of analyte present in the original sample, typically by using a relationship determined from standard samples containing known amounts of analyte of interest in the range expected for the sample to be tested. Typically, the detection product incorporates one or more detectable labels, which are provided by one or more assay reagents. Examples of commonly used labels include radioactive isotope labels, such as $^{125}I$ and $^{32}P$; enzyme (e.g., peroxidase, β-galactosidase) and enzyme substrate labels; fluorescent labels (e.g., fluorosceines, rhodamines); electron-spin resonance labels (e.g., nitroxide free radicals); immunoreactive labels (e.g., antibodies, antigens); and labels which are one member of a binding pair (e.g., biotin-avidin, biotin-streptavidin). Sandwich assays typically involve forming a complex in which the analyte of interest is sandwiched between one assay reagent which is ultimately used for separation (e.g., antibody, antigen, one member of a binding pair) and a second assay reagent which provides a detectable label. Competition assays typically involve a system in which both the analyte of interest and an analog of the analyte compete for a binding site on another reagent (e.g., an antibody), wherein one of the analyte, analog, or binding reagent possess a detectable label.

Recently, ECL labels have become more common in chemical and biological assays. For example, ECL labels (e.g., those containing a $Ru(bpy)_3^{2+}$ moiety) can be modified by attaching reactive groups (e.g., to one or more of the bipyridyl ligands) to form activated labeling reagents for proteins, nucleic acids, and other molecules. This approach offers many advantages over other detection systems, such as $^{32}P$ radiolabeling, including, but not limited to, many of the following: (1) the absence of radioactive isotopes thereby reducing the problems associated with sample handling and disposal; (2) very low detection limits for the ECL label, often as low as 0.2 picomolar ($2\times10^{-13}$ M), since each label can emit several photons per measurement cycle; (3) a dynamic range for label quantification which often extends over six orders of magnitude; (4) extremely stable labels often with long shelf lives; (5) low molecular weight labels (~1000 atomic units) which may be coupled to proteins, oligonucleotides, etc., often without affecting immunoreactivity, solubility, ability to hybridize, etc.; (6) high selectivity and low background, since the ECL reaction sequence is initiated electrochemically and only those species with appropriate electrochemical properties in the proximity of the electrode are detected; and (7) simple and rapid measurement, typically requiring only a few seconds.

In recent years, ECL has been exploited in the development of immunoassays and DNA probe analysis. See, for example, Blackburn et al., 1991, Kenten et al., 1991, 1992, Leland et al., 1992, and Yost, 1993.

In a typical and well known DNA separation assay employing ECL, the target oligonucleotide is amplified (e.g., using PCR) using a biotin-containing primer oligonucleotide to yield an increased concentration of target oligonucleotides which comprise a biotin moiety; an excess of an oligonucleotide hybridization probe to which is attached an ECL label, and which hybridizes to the target oligonucleotides to form hybridized probe-target duplexes, is then added; streptavidin coated beads, which strongly and selectively bind the biotin-containing duplexes, are added; the beads are separated from the mixture (e.g., magnetically, gravimetrically), thereby removing the excess labeled oligonucleotide hybridization probe; and the target oligonucleotide, which is bound to the beads and which is hybridized to an ECL-labeled hybridization probe, is detected and/or quantified using ECL.

Blackburn et al. (1991) apparently disclose the use of an N-succinimidyl ester derivative of $Ru(bpy)_3^{2+}$ as a means for attaching an ECL label to an oligonucleotide hybridization probe. By using a biotin-labeled oligonucleotide primer, the polymerase chain reaction ("PCR") amplification products could be separated by binding to streptavidin coated magnetic beads. Once separated, the $Ru(bpy)_3^{2+}$ labeled oligonucleotide probe was hybridized to the bound PCR products, and detected by ECL.

Kenten et al. (1991) apparently similarly disclose the use of ECL assays of PCR amplified products from oncogenes, viruses, and cloned genes. In one assay, a $Ru(bpy)_3^{2+}$ label was attached to one or both of the oligonucleotide primers; following amplification, binding, and separation, the PCR products were detected by ECL. In another assay, an oligonucleotide probe having an attached $Ru(bpy)_3^{2+}$ label was hybridized to magnetic bead-bound PCR products, the excess probe was removed by washing, and the hybridized product detected by ECL. In a third assay, an oligonucleotide probe having an attached $Ru(bpy)_3^{2+}$ label was hybridized to unbound PCR products, the hybridized product was bound to magnetic beads, the excess probe was removed by washing, and the hybridized product detected by ECL. In each case, the desired product was detected by the presence of an ECL label.

Kenten et al. (1992) apparently disclose "binding assays" which employ ECL labels. Apparently, a complex comprising the analyte of interest, an ECL label, and particle is formed, and the presence of this complex is subsequently detected by ECL.

Chemical and biological assays may often be conveniently classified as "separation assays" or "non-separation assays." Generally, in separation assays, the detection product(s) is physically separated from other products and/or unreacted analyte of interest and unreacted assay reagents. (For example, it is often necessary to physically separate the detection product so that only those labels which are part of the detection product are detected, and not those of the excess labeling reagent.) The amount of analyte may then be determined either directly from the amount of labeled detection product, or indirectly from the amount of unused labeling reagent. Separation may often be achieved by exploiting a selective binding reaction between members of a binding pair (e.g., biotin-avidin, antibody-antigen, oligonucleotide hybridization probe-oligonucleotide). For example, a labeled detection product having one member of a binding pair may be first formed in a fluid phase (e.g., in solution), and separation may then be effected, for example, by capture of the ECL labeled detection product by a solid phase reagent having the other member of the binding pair; the detection product may then be recovered by washing the solid phase free of unreacted analyte and reagents. Many other separation strategies employing binding pairs are well known in the art.

Assays which do not require a separation step are highly desirable, as they typically require less sample manipulation and are often readily adapted to "real time" assays. Such assays may often be conveniently classified as "non-separation assays." In non-separation assays, the detection product is typically not physically separated from unused assay reagents and unused analyte. Instead, the presence of the detection product is typically detected by a property which at least one of the assay reactants acquires or loses only as a result of contacting the analyte of interest. A number of such non-separation assays have been developed.

In one example of a non-separation assay, both an enzyme and an enzyme inhibitor is used. Upon contacting the analyte of interest, the enzyme and enzyme inhibitor are either brought together (to reduce enzyme activity) or separated (to increase enzyme activity). Any change in enzyme activity is then correlated with the presence and/or amount of the analyte of interest. See, for example, Yoshida et al., 1980, and Zuk et al., 1980.

In another example of a non-separation assay, both a chromophore and a chromophore modifier is used. Again, upon contacting the analyte of interest, the chromophore and chromophore modifier are either brought together or separated, thereby yielding a change in color or a change in intensity of a specified color. Any change in color and/or intensity of color is then correlated with the presence and/or amount of the analyte of interest. See, for example, Zuk et al., 1980.

In yet another example of a non-separation assay, both a fluorophore and a fluorophore quencher is used. Upon contacting the analyte of interest, the fluorophore and fluorophore quencher are either brought together (to reduce fluorescence) or separated (to increase fluorescence). See, for example, Ullman et al., 1976; Ullman, 1979; Zuk et al., 1981; and Ullman et al., 1981. More recent examples of photoluminescence assays (e.g., fluorescence assays) which exploit photoluminescence quenchers are discussed below.

Tyagi et al. (1996) apparently disclose an assay for oligonucleotides which employs a particular oligonucleotide probe (referred to as a "molecular beacon") which possesses both a fluorophore (i.e., a label) and a fluorescence quencher. In the absence of the target oligonucleotide, portions of the oligonucleotide probe hybridize with itself, bringing the fluorophore and the fluorescence quencher into close proximity; in this form, no fluorescence signal is observed. In the presence of the target oligonucleotide, the oligonucleotide probe de-hybridizes and preferentially hybridizes with the target oligonucleotide, and in doing so, separates the fluorophore and the fluorescence quencher; in this form, a fluorescence signal is observed. Thus, fluorescence is only observed from those oligonucleotide probes which are hybridized with the target oligonucleotide. In this way, it is not necessary to remove the unhybridized oligonucleotide probes prior to measuring the fluorescence signal.

Heid et al. (1996) apparently disclose a real-time quantitative assay for DNA analysis using dual-labeled fluorogenic hybridization probes. An oligonucleotide probe is prepared having a first fluorescent dye (FAM, 6-carboxyfluorescein) which acts as a reporter, and a second fluorescent dye (TAMRA, 6-carboxy-tetramethylrhodamine) which quenches the emission spectra of the first fluorescent dye. The 5'-specific exo-nuclease activity of the Taq polymerase causes only those probes which have hybridized with a target oligonucleotide to be degraded, releasing the two dyes, and resulting in an increase in the FAM fluorescent emission.

Wittwer et al. (1997) apparently disclose methods for continuous fluorescence monitoring of PCR products during amplification. In one assay, commercially available dual labeled oligonucleotide probes possessing both a "donor" moiety (e.g., fluorescein) and an "acceptor" moiety (e.g., rhodamine) are hybridized to a target oligonucleotide. The close proximity of the acceptor apparently attenuates the fluorescence signal from the donor. A polymerase having 5'-specific exo-nuclease activity is added, and, during polymerization, the oligonucleotide probe is degraded, releasing both the donor and the acceptor. No longer in close proximity to the acceptor, the donor then yields an increased fluorescence signal. In another assay, based on resonance energy transfer, two different oligonucleotide probes were prepared, one having a "donor" moiety (e.g., fluorescein) and one having an "acceptor" moiety (e.g., the cyanine dye Cy5®). The two oligonucleotide probes were selected so that, when hybridized to the target oligonucleotide, the donor and acceptor moieties are brought into close proximity. When the donor is photoexcited, some or all of its energy is transferred to the acceptor, and the fluorescence signal from the acceptor increases. (See also, for example, Maliwal, et al., 1995). In this way, the target oligonucleotide is detected and quantified by an increase in the fluorescence signal from the acceptor.

Unlike the quenching of ECL, the quenching of photoluminescence has been widely studied, and many compounds are known to quench photoluminescence under a variety of conditions. In sharp contrast, only a few compounds are known to efficiently quench ECL, and many of those which are well known (e.g., methylviologen carboxylate) either only poorly quench ECL or are impractical for use in assays.

The inventors have discovered that certain other classes of compounds strongly quench ECL, such as compounds comprising at least one benzene moiety, and, more particularly, compounds comprising at least one phenol moiety, quinone moiety, benzene carboxylic acid, and/or benzene carboxylate moiety.

The ECL properties of such compounds have not been widely studied. The use of strongly fluorescent compounds, such as anthracenes, to increase ECL emission is known, and indeed widely used in the common ECL assays. Chmura et al. (1994) apparently examined assays for antioxidants and free radical scavengers, such as citrate, which relied on these compounds' ability to quench of anthracene-sensitized ECL. Kricka et al. (1991) apparently describe the use of p-iodophenol as a chemiluminescence enhancer, rather than a quencher. Hill et al. (1988) apparently examined the ECL emission from a number of dansylated derivatives in an effort to adapt ECL to reverse-phase liquid chromatography (RPLC). They apparently examined the effect of the dansyl group (i.e., 5-dimethylamino-1-naphthalanesulfonyl), which is a well known fluorescent label, on the ECL emission of a number of amino acids and phenolic compounds, and found that the presence of a dansyl group increased the ECL emission of many of the compounds tested. In their study of the ECL of osmium complexes, Abruna et al. (1985) apparently describe the quenching of ECL of an Os(bpy)$_2$diphos$^{+2}$ species by a ferricenium species (the oxidized form of a ferrocene; a species comprising two cyclopentadienyl ions (i.e., $C_5H_5^-$) and a sandwiched ferrous (i.e., $Fe^{+2}$) ion.

Using the efficient ECL quenchers disclosed herein, assays may be developed which employ an ECL label and an ECL quencher and which permit, inter alia, assays such as non-separation assays which offer many, if not all, of the advantages offered by ECL detection methods over other detection methods. Thus, the present invention broadly pertains to certain classes of chemical moieties which strongly quench ECL, and the use of these ECL quenchers, for example, in ECL assays which employ an ECL label and an ECL quencher. One class of such quenching moieties are those which comprise at least one benzene moiety. Sub-classes of such quenching moieties are those which comprise at least one phenol moiety, quinone moiety, benzene carboxylic acid, and/or benzene carboxylate moiety.

BRIEF DESCRIPTION OF THE INVENTION

The present invention generally pertains to certain classes of chemical moieties which strongly quench ECL, and the use of these ECL quenchers in combination with ECL labels, for example, in ECL assay methods which employ an ECL quencher and an ECL label. One class of such quenching moieties are those which comprise at least one benzene moiety. Sub-classes of such quenching moieties are those which comprise at least one phenol moiety, quinone moiety, benzene carboxylic acid, and/or benzene carboxylate moiety.

One aspect of the present invention pertains to a method for detecting an analyte in a sample composition comprising the steps of: (a) preparing an assay mixture comprising: said sample composition; a reagent having an ECL label; and, a reagent having an ECL quenching moiety, said ECL quenching moiety comprising at least one benzene moiety; (b) determining any difference between the ECL emissions of: (i) the assay mixture prepared in step (a); and, (ii) an assay mixture comprising: said reagent having an ECL label; said reagent having an ECL quenching moiety; and a known amount of said analyte; and, (c) correlating any difference determined in step (b) with the amount of analyte in said sample.

In one embodiment, said ECL quenching moiety comprises at least one moiety selected from the group consisting of phenol moieties, quinone moieties, benzene carboxylic acid moieties, and benzene carboxylate moieties. In one embodiment, said ECL quenching moiety comprises at least one phenol moiety. In one embodiment, said ECL quenching moiety comprises at least one quinone moiety. In one embodiment, said ECL quenching moiety comprises at least one benzene carboxylic acid moiety. In one embodiment, said ECL quenching moiety comprises at least one benzene carboxylate moiety.

In one embodiment, said ECL label comprises ruthenium. In one embodiment, said ECL label comprises osmium. In one embodiment, said ECL label comprises a polyaromatic hydrocarbon.

In one embodiment, said analyte comprises an oligonucleotide. In one embodiment, said analyte comprises DNA. In one embodiment, said analyte comprises RNA. In one embodiment, said analyte comprises a polypeptide. In one embodiment, said analyte comprises an antibody. In one embodiment, said analyte comprises an antigen. In one embodiment, said analyte comprises an enzyme. In one embodiment, said analyte comprises an enzyme substrate. In one embodiment, said analyte comprises a polysaccharide.

In one embodiment, said known amount of analyte is zero.

In one embodiment, said reagent having an ECL label and said reagent having an ECL quenching moiety are the same reagent. In one embodiment, said reagent having an ECL label and said reagent having an ECL quenching moiety are different reagents.

In one embodiment, the method further comprises the steps of: conducting a chemical reaction on a substrate present in an initial sample composition to produce said analyte in said sample composition prior to step (a); and, correlating any difference determined in step (b) with the amount of substrate in said initial sample composition. In one embodiment, the method further comprises the step of: conducting a chemical reaction with the assay mixture prepared in step (a) before the determining of step (b).

Another aspect of the present invention pertains to an assay reagent for use in the assay methods of the present invention, said assay reagent comprising an ECL quenching moiety, said assay reagent provided in a suitable container. In one embodiment, the assay reagent comprises an ECL quenching moiety and an ECL label, said assay reagent provided in a suitable container.

Still another aspect of the present invention pertains to an assay reagent kit for use in the assay methods of the present invention, said assay reagent kit comprising an assay reagent in a suitable container, said assay reagent comprising an ECL quenching moiety, and instructions for performing said method. In one embodiment, the assay reagent kit comprises an assay reagent in a suitable container, said assay reagent comprising an ECL quenching moiety and an ECL label, and instructions for performing said method.

As will become apparent, preferred features and characteristics of one aspect of the invention are applicable to any other aspect of the invention.

DETAILED DESCRIPTION OF THE INVENTION

Figure 1:
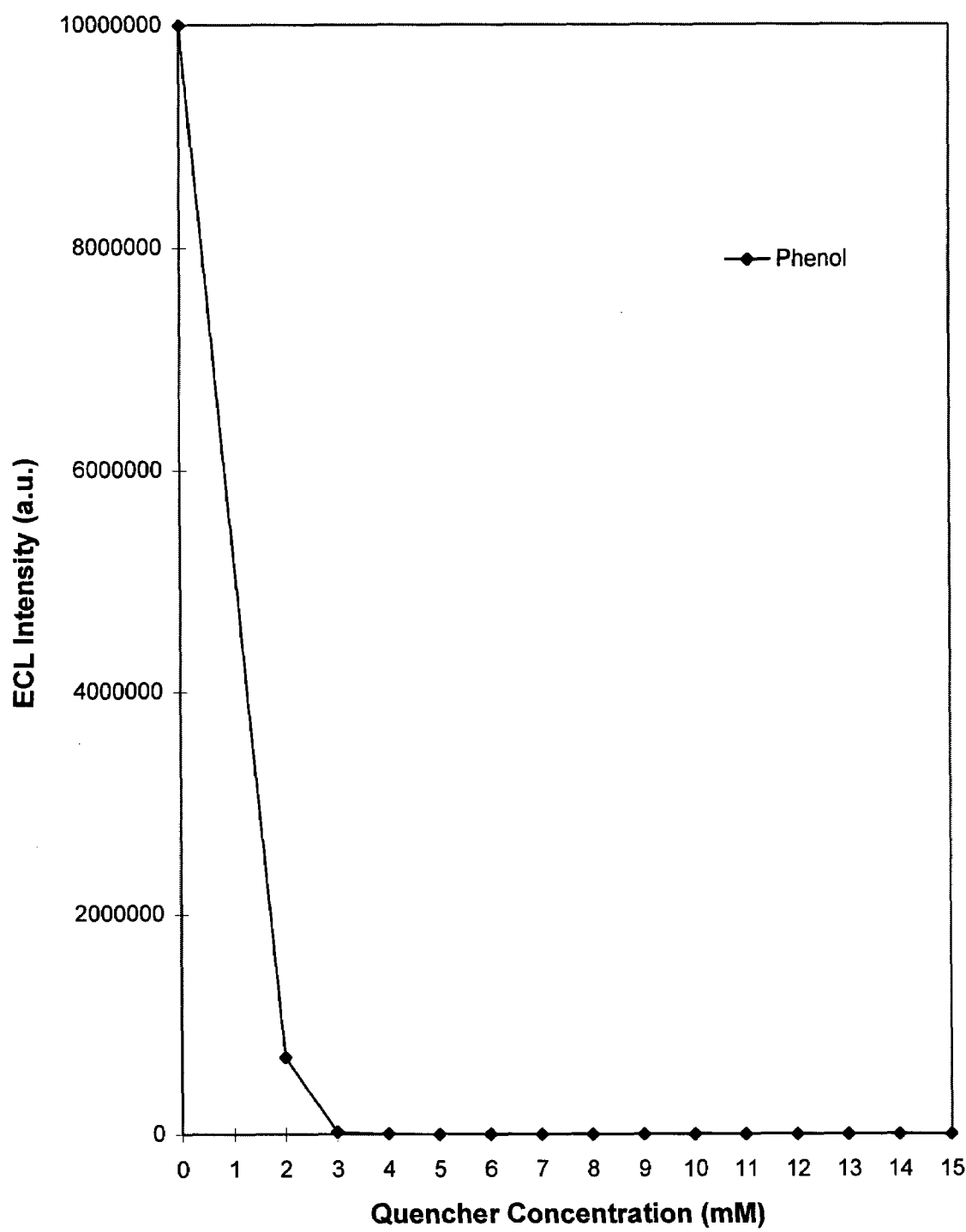
FIG. 1 is a graph depicting $Ru(bpy)_3^{+2}$/TPAH ECL intensity versus concentration of phenol (as a quenching agent), as described in Example 1 below.

The present invention generally pertains to certain classes of chemical moieties which strongly quench ECL, and the use of these ECL quenchers in combination with ECL labels, for example, in ECL assays which employ an ECL quencher and an ECL label.

A. Electrochemiluminescent Labels

As described above, ECL is the emission of photons of electromagnetic radiation (e.g., light) from an electronically excited chemical species which has been generated electrochemically.

The terms "electrochemiluminescent label" and "ECL label," as used herein, pertain to a chemical moiety which has electrochemiluminescent properties. More specifically, an ECL label is a chemical moiety which can be electrochemically converted to an electronically excited species which, either directly or upon further chemical reaction, emits one or more photons (e.g., light) as it relaxes to a lower energy state.

A number of chemical moieties may serve as an ECL label. An important class of such moieties are derived from metal chelates, which comprise one or more metal ions, which may be the same or different, and one or more ligands, which may be the same or different.

In one embodiment, the metal ion of the metal chelate is selected from the group consisting of transition metal ions and rare earth metal ions in any of their oxidation states. In another embodiment, the metal ion is selected from the group consisting of ions of ruthenium, osmium, rhenium, iridium, rhodium, platinum, indium, palladium, molybdenum, technetium, copper, chromium and tungsten in any of their oxidation states. In another embodiment, the metal ion is selected from the group consisting of ions of ruthenium and osmium in any of their oxidation states.

Ligands of the metal chelate may be monodentate or polydentate and may be organic (i.e., comprising at least one carbon atom) or inorganic. Examples of monodentate ligands include carbon monoxide (i.e., CO), cyanide ion (i.e., CN⁻), isocyanide ion (i.e., NC⁻), halides (e.g., F⁻, Cl⁻, Br⁻, I⁻), phosphines (e.g., $PR_3$), amines (e.g., $NR_3$), stilbenes (e.g., $SbR_3$), and arsines (e.g., $AsR_3$). Examples of polydentate ligands include aromatic heterocyclic ligands such as nitrogen-containing aromatic heterocyclic ligands. Examples of nitrogen-containing aromatic heterocyclic ligands include unsubstituted and substituted bipyridyls, bipyrazyls, terpyridyls, and phenanthrolyls. Examples of substituents include $C_{1-6}$ alkyl, substituted $C_{1-6}$ alkyl, $C_{6-15}$ aryl and heteroaryl, substituted $C_{6-15}$ aryl and heteroaryl, $C_{7-15}$ aralkyl and heteroaralkyl, substituted $C_{7-15}$ aralkyl and heteroaralkyl, carboxy (i.e., —COOH), carboxylate (i.e., —COO⁻), carboxyesters (i.e., —COOR, such as the N-hydroxysuccinimidyl ester) carboxaldehyde (i.e., —CHO), carboxamide (i.e., —CONH₂), hydroxy (i.e., —OH), cyano (i.e., —CN), isocyano (i.e., —NC), amino (i.e., —NH₂), imino (i.e., =NH), sulfhydryl (i.e., —SH), and phosphino (i.e., —PH₂).

In one embodiment, the ECL label is derived from a tris(2,2'-bipyridyl) ruthenium (II) cation, $Ru(bpy)_3^{2+}$, shown below, or a derivative thereof.

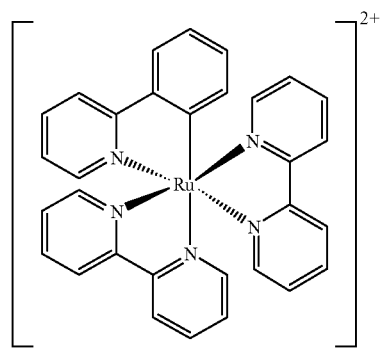

Salts of $Ru(bpy)_3^{2+}$ and its derivatives are usually very stable, water soluble compounds that can be chemically modified to possess reactive groups (i.e., to form chemically activated species). For example, one or more reactive groups may be attached to one or more of the bipyridyl ligands, which then permit the attachment of the Ru(bpy)$_3^{2+}$-like moiety (as an ECL label) to other molecules. See, for example, Bard et al, 1993 and Blackburn et al., 1991.

For example, one of the three bipyridyl ligands may be derivatized to possess an N-succinimidyl ester of a carboxylic acid group attached to one of the bipyridyl ligands via a linker group. Such a compound is 4-(N-succinimidyloxycarbonylpropyl)-4'-methyl-2,2'-bipyridine bis(2,2'-bipyridine) ruthenium(II) dihexafluorophosphate), the cation of which is shown below, and which is commercially available from IGEN Inc. (Rockville, Md.) under the product name Origen® ECL label. This activated ester, shown below, permits the easy attachment of the Ru(bpy)$_3^{2+}$-like ECL label to molecules which possess, for example, an amine group (e.g, —NH$_2$).

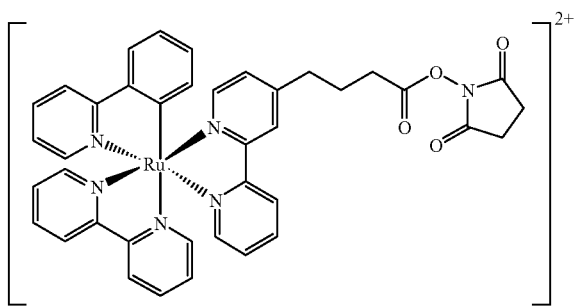

In another example, one of the three bipyridyl ligand may be derivatized to possess a maleimide group, optionally via a linker group. This may be achieved, for example, by reacting an active ester derivative, such as that shown above, with a maleidmido-alkylamine (e.g., maleimidoethylamine). Such a compound is 4-(maleimido-ethylamino-carbonylpropyl)-4'-methyl-2,2'-bipyridine bis(2,2'-bipyridine) ruthenium(II) dihexafluorophosphate, the cation of which is shown below. This maleimide permits the easy attachment of the Ru(bpy)$_3^{2+}$-like ECL label to molecules which possess, for example, a thiol group (e.g., —SH).

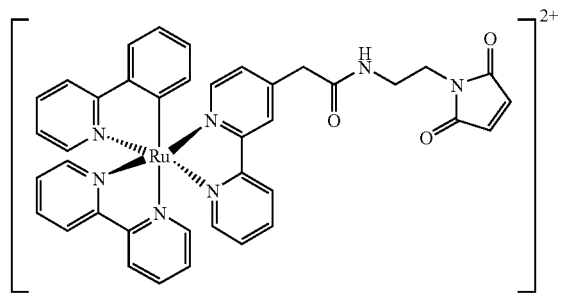

Other examples of metal chelates from which Ru(bpy)$_3^{2+}$-like ECL labels may be derived include:

bis[(4,4'-carbomethoxy)-2,2'-bipyridine]-2-[3-(4-methyl-2,2'-bipyridine-4'-yl) propyl]-1,3-dioxolane ruthenium (II);

bis(2,2'-bipyridine)-[4-(butan-1-al)-4'-methyl-2,2'-bipyridine-] ruthenium (II);

bis(2,2'-bipyridine)-[4-(4'-methyl-2,2'-bipyridine4'-yl)-butyric acid] ruthenium (II);

bis(2,2'-bipyridine)-[4-(4'-methyl-2,2'-bipyridine)-butyl) amine] ruthenium (II);

bis(2,2'-bipyridine)[1-bromo-4(4'-methyl-2,2'-bipyridine) 4'-yl)butane] ruthenium (II); and bis[(2,2'-bipyridine)maleimidohexanoic acid]-4-methyl-2,2'-bipyridine-4'-butylamide ruthenium (II).

Other examples of metal chelates from which ECL labels may be derived include other 2,2'-bipyridyl complexes, such as Os(bpy)$_3^{2+}$ and derivatives thereof, phenanthroline (phen) and derivatives thereof; other transition metal fluorophores, such as tricarbonyl(chloro)(1,10-phenanthroline) rhenium(I), square planer platinum(II) complexes, Cr(bpy)$_3^{2+}$; multinuclear complexes such as Pt$_2$(diphosphonate)$_4^{4-}$; and clusters such as Mo$_6$Cl$_{12}^{2-}$.

Another important class of chemical moieties which may serve as an ECL label are those derived from polyaromatic hydrocarbons, such as naphthalene, anthracene, 9,10-diphenylanthracene, phenanthrene, pyrene, chrysene, perylene, coronene, rubrene, and the like, and from organic laser dyes, such as fluoresceine, rhodamine, and the like, which are able to emit light upon electrochemical excitation.

Typically, one or more ECL labels are attached (e.g., conjugated) to another molecule (e.g., an antibody, an oligonucleotide probe). ECL labels may be attached to molecules (to form labeled molecules) using standard synthetic methods which are well known to one of skill in the art. For example, as discussed above, a molecule comprising an ECL label (e.g., Ru(bpy)$_3^{2+}$or a derivative thereof) may be derivatized to form a chemically activated species (e.g., an activated ester, a maleimide) which may then be reacted with, and thus covalently bound to, a molecule (e.g., to yield a labeled assay reagent).

B. Quenching Moieties

As described above, ECL is the emission of photons of electromagnetic radiation (e.g., light) from an electronically excited chemical species which has been generated, either directly or indirectly, electrochemically. The observed ECL emission may be partially or completed attenuated by a quenching moiety which is in quenching contact with an ECL label. The terms "quenching moiety" and "quencher" as used herein, pertain to a chemical moiety which, when in quenching contact with an ECL label, attenuates the observed ECL emission.

The phrase "in quenching contact with," as used herein, pertains to the condition wherein the observed ECL emission from an ECL label is attenuated by the presence of an ECL quenching moiety. A quenching moiety in quenching contact with an ECL label attenuates the observed ECL emission from that label by at least 10%. Preferably, a quenching moiety in quenching contact with an ECL label attenuates the observed ECL emission from that label by at least 20%, more preferably by at least 30%, still more preferably by at least 40%, yet more preferably by at least 50%. Typically, a quenching moiety in quenching contact with an ECL label is physically present in spatial proximity to the ECL label. For example, a quenching moiety in quenching contact with an ECL label is typically separated from an ECL label by a distance of less than about 100 nm, more typically less than about 50 nm, still more typically less than about 30 nm, yet more typically less than about 10 nm. Using well known and standard methods, one of skill in the art may readily determine whether a prospective quenching moiety will in fact attenuate the observed ECL emission and also whether or not a specified quenching moiety is, in fact, in quenching contact with an ECL label.

Without wishing to be bound to any particular theory, Applicants note that a number of possible mechanisms for the quenching effect have been postulated. In one mechanism, the electronically excited label relaxes by transferring an electron to the quencher (perhaps by quantum mechanical tunneling), to yield an electronically excited quencher, which relaxes non-radiatively (e.g., vibrationally, rotationally). In another mechanism, the electronically excited label relaxes by emitting a photon which is absorbed by the quencher, to yield an electronically excited quencher, which again relaxes non-radiatively. In still another mechanism, the quenching moiety is electrochemically converted to an electro-oxidation or electro-reduction product (typically during the ECL measurement), and this product (or subsequent reaction product) quenches the ECL, for example, by one of the preceding mechanisms. In yet another mechanism, the quenching moiety, or an electro-oxidation or electro-reduction product of the quenching moiety (or subsequent reaction product) acts as a free radical scavenger and intercepts one or more species involved in the ECL reaction sequence (e.g., TPA* may be intercepted prior to reaction with Ru(bpy)$_3^{3+}$, preventing the formation of Ru(bpy)$_3^{2+}$*) and thus quenching the ECL.

A number of chemical moieties may serve as a quenching moiety. An important class of such quenching moieties are those which comprise at least one benzene moiety. A sub-class of preferred quenching moieties are those which comprise at least one phenol moiety. Another sub-class of preferred quenching moieties are those which comprise at least one quinone moiety (i.e., a 1,4-benzoquinone or a 1,2-benzoquinone). Yet another sub-class of preferred quenching moieties are those which comprise at least one benzene carboxylic acid or benzene carboxylate moiety.

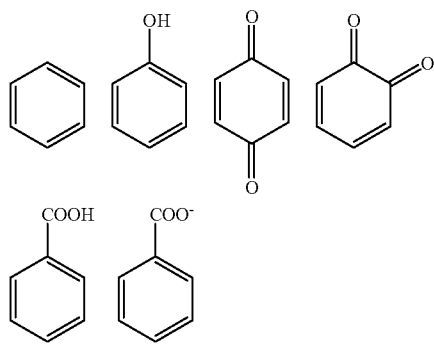

The term "quenching agent," as used herein, pertains to a chemical compound which comprises a quenching moiety. Examples of quenching agents which comprise at least one phenol moiety, and from which quenching moieties comprising at least one phenol moiety may be derived, include, but are not limited to:

phenol;

alkyl-phenols, such as $C_{1-6}$ alkyl-phenols including o-alkyl-phenol, m-alkyl-phenol, and p-alkyl-phenol, such as o-methyl-phenol (i.e., o-cresol), m-methyl-phenol (i.e., m-cresol), p-methyl-phenol (i.e., o-cresol), o-ethyl-phenol, m-ethyl-phenol, p-ethyl-phenol, o-propyl-phenol, m-propyl-phenol, and p-propyl-phenol;

aryl-phenols, such as $C_{7-10}$ aryl-phenols, including o-aryl-phenol, m-aryl-phenol, and p-aryl-phenol, such as p-phenyl-phenol;

halo-phenols, including o-halo-phenol, m-halo-phenol, and p-halo-phenol, such as o-fluoro-phenol, m-fluoro-phenol, and p-fluoro-phenol;

hydroxy-phenols, including o-hydroxy-phenol (i.e., catechol), m-hydroxy-phenol (i.e., resorcinol), and p-hydroxy-phenol (i.e., hydroxyquinone); and biphenols, such as 4,4'-biphenol.

Examples of quenching agents which comprise at least one quinone moiety, and from which quenching moieties comprising at least one quinone moiety may be derived, include, but are not limited to:

quinones (i.e., benzoquinones), such as o-quinone (i.e., 1,2-benzoquinone) and p-quinone (i.e., 1,4-benzoquinone);

alkyl-quinones, such as $C_{1-6}$ alkyl-quinones including $C_{1-6}$ alkyl-1,4-benzoquinones, such as 2-methyl-1,4-benzoquinone, 2-ethyl-1,4-benzoquinone, 2-n-propyl-1,4-benzoquinone, 2,6-dimethyl-1,4-benzoquinone, and 2,5-dimethyl-1,4-benzoquinone;

halo-quinones, such as halo-1,4-benzoquinones, including 2-fluoro-1,4-benzoquinone, 2-chloro-1,4-benzoquinone, 2-bromo-1,4-benzoquinone, 2-iodo-1,4-benzoquinone, 2,6-difluoro-1,4-benzoquinone, 2,5-difluoro-1,4-benzoquinone; 2,6-dichloro-1,4-benzoquinone, 2,5-dichloro-1,4-benzoquinone; 2,6-dibromo-1,4-benzoquinone, and 2,5-dibromo-1,4-benzoquinone;

naphthoquinones, such as 1,2-napththoquinones and 1,4-naphthoquinones, including 2-methoxy-3-methyl-1,4-naphthoquinone;

anthraquinones, such as 1,2-anthraquinones, 1,4-anthraquinones, 9,10-anthraquinones, including 1,5-dihydroxy-9,10-anthraquinone, 1,2,3,4-tetrafluoro-5,8-dihydroxy-9,10-anthraquinone, 9,10-anthraquinone-2-carboxylic acid, 9,10-anthraquinone-2-sulfonic acid, 9,10-anthraquinone-1,5-disulfonic acid, and 9,10-anthraquinone-2,6-disulfonic acid.

Examples of quenching agents which comprise at least one benzene carboxylic acid or benzene carboxylate moiety, and from which quenching moieties comprising at least one benzene carboxylic acid or benzene carboxylate moiety may be derived, include, but are not limited to:

benzoic acid;

aminobenzoic acids, such as o-aminophenol, m-aminophenol, and p-aminophenol;

hydroxybenzoic acids, such as o-hydroxyphenol, m-hydroxyphenol, and p-hydroxyphenol; and nitrobenzoic acids, such as o-nitrophenol, m-nitrophenol, and p-nitrophenol.

In one embodiment, the quenching moiety is a quinone or a derivative thereof. Quinone and its derivatives may usually be chemically modified to possess reactive groups (i.e., to form chemically activated species). For example, on one or more reactive groups may be attached (e.g., at the ortho- or meta-positions of 1,4-benzoquinone) optionally via a linker group, which then permits the attachment of the quinone-like moiety (as a quenching moiety) to other molecules.

For example, a 1,4-benzoquinone may be derivatized to possess a carboxylic acid group (i.e., —COOH) attached to an ortho- or meta-carbon via a linker group, such as an alkyl group. Such a compound is 2-(1-carboxy-but-2-yl)-5-methyl-1,4-benzoquinone. This carboxylic acid derivative may be derivatized to form the N-succinimidyl ester (shown below), which permits the easy attachment of the quinone-like quenching moiety to molecules which possess, for example, an amino group.

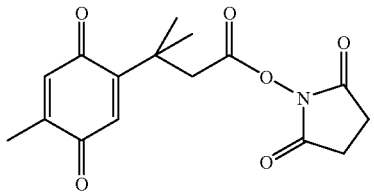

Quenching moieties may be attached to molecules using standard and well known synthetic methods. For example, as discussed above, a molecule comprising a quenching moiety (e.g., benzene or a derivative, such as phenol, quinone, benzene carboxylic acid, benzene carboxylate) may be derivatized to form a chemically activated species (e.g., an active ester, a maleimide) which may then be reacted with, and thus covalently bound to, a molecule.

C. Assays Employing an ECL Label and an ECL Quencher

The present invention provides new assay methods for detecting, and preferably quantifying, one or more analytes of interest which are present in a sample composition. The terms "assay" and "assay method," as used herein, pertain to a method of detecting the presence of (e.g., qualitative assay), and preferably quantifying (e.g., quantitative assays), one or more analytes of interest.

Assays of the present invention generally involve contacting the analyte of interest (which is typically one component of a sample composition) with a pre-determined non-limiting amount of one or more assay reagents, measuring the ECL properties of a resulting product (the detection product(s)), and correlating the measured ECL with the amount of analyte present in the original sample, typically by using a relationship determined from standard samples containing known amounts of analyte of interest in the range expected for the sample to be tested. In a qualitative assay, simply determining whether the measured ECL is above or below a threshold value (established, for example, using samples known to contain or be free of analyte of interest) may be sufficient to establish the assay result. Thus, unless otherwise required, the term "measuring" can refer to either qualitative or quantitative determination. Assays of the present invention may be heterogeneous (separation) assays or homogeneous (non-separation) assays.

The terms "analyte" and "analyte of interest," as used herein, pertain to a substance which is to be detected and preferably quantified. Analytes may be inorganic or organic, though typically they are organic. Analytes may be naturally occurring or synthetic. Examples of classes of organic analytes include biological molecules such as amino acids, proteins, glycoproteins, lipoproteins, saccharides, polysaccharides, lipopolysaccharides, fatty acids, and nucleic acids. Examples of organic analytes include antibodies, antigens, haptens, enzymes, hormones, steroids, vitamins, oligonucleotides, and pharmacological agents.

The terms "sample" and "sample composition," as used herein, pertain to a composition which comprises one or more analytes of interest, or which may be processed to comprise one or more analytes of interest. The sample may be in solid, emulsion, suspension, liquid, or gas form. Typically, the sample is processed (e.g., by the addition of a liquid electrolyte) so as to be a fluid (i.e., free flowing) form (e.g., emulsion, suspension, solution) in order to readily permit and simplify the detection and quantification of the analytes of interest using ECL methods. Typically, the analyte of interest is present in the sample composition at a concentration of $10^{-3}$ M (micromolar) or less, for example, often as low as $10^{-12}$ M (picomolar), and even as low as $10^{-13}$ M (sub-picomolar).

The assays of the present invention may be characterized as ECL assays; that is, in the assays of the present invention, the presence of analytes of interest, and preferably the quantity of analytes of interest, is determined using ECL. Furthermore, the assays of the present invention rely on the use of ECL label in combination with certain classes of ECL quenchers. One class of such quenching moieties are those which comprise at least one benzene moiety. Sub-classes of such quenching moieties are those which comprise at least one phenol moiety, quinone moiety, benzene carboxylic acid, and/or benzene carboxylate moiety, as described above.

Thus, the present invention provides methods for detecting an analyte in a sample composition comprising the steps of:

(a) preparing an assay mixture comprising:
 said sample composition;
 a reagent having an ECL label; and
 a reagent having an ECL quenching moiety, said ECL quenching moiety comprising at least one benzene moiety;

(b) determining any difference between the ECL emissions of
 (i) the assay mixture prepared in step (a); and
 (ii) an assay mixture comprising:
  said reagent having an ECL label;
  said reagent having an ECL quenching moiety; and
  a known amount of said analyte; and (c) correlating any difference determined in step (b) with the amount of analyte in said sample.

In one embodiment, said ECL quenching moiety comprises at least one moiety selected from the group consisting of phenol moieties, quinone moieties, benzene carboxylic acid moieties, and benzene carboxylate moieties, as described above. In another embodiment, said ECL quenching moiety comprises at least one phenol moiety. In another embodiment, said ECL quenching moiety comprises at least one quinone moiety. In another embodiment, said ECL quenching moiety comprises at least one benzene carboxylic acid moiety. In another embodiment, said ECL quenching moiety comprises at least one benzene carboxylate moiety.

In one embodiment, said known amount of analyte is zero.

In one embodiment, said reagent having an ECL label and said reagent having an ECL quenching moiety are the same reagent. In another embodiment, said reagent having an ECL label and said reagent having an ECL quenching moiety are different reagents.

In one embodiment, the method further comprises the initial step of conducting a chemical reaction on a substrate present in an initial sample composition to produce said analyte in said sample composition, and the final step of correlating any difference determined in step (b) with the amount of substrate in said initial sample composition.

In one embodiment, the method further comprises the step of conducting a chemical reaction with the assay mixture prepared in step (a) before the determining of step (b).

In one embodiment, the presence of a particular analyte of interest results in a decrease in ECL emission resulting from, for example, a decrease in a particular ECL emission from an ECL label. Such a change in ECL emission may result, for example, by introducing a quenching moiety into quenching contact with an ECL label. Alternatively, in another embodiment, the presence of a particular analyte of interest result in an increase in ECL emission resulting from, for example, an increase in a particular ECL emission from an ECL label. Such a change in ECL emission may result, for example, by removing a quenching moiety from quenching contact with an ECL label.

In one embodiment, the assays of the present invention exploit binding pairs in order to bring ECL labels and ECL quenching moieties together (into quenching contact) or apart (out of quenching contact). Examples of binding pairs include oligonucleotides and oligonucleotide hybridization probes; antibodies and antigens; enzymes and substrates; and strong binding pairs such as biotin-avidin. Such binding pairs may typically be employed in assays of the present invention to permit the detection an analyte of interest which is one member of a binding pair, or which is conjugated to one member of a binding pair.

In one embodiment, the assays of the present invention may be employed to detect oligonucleotides (e.g., DNA, RNA). Deoxyribonucleic acid (DNA) is a polynucleotide, more specifically, a polymer of deoxyribonucleotide units. A deoxyribonucleotide typically consists of a nitrogenous base, a sugar, and one or more phosphate groups. A deoxyribonucleoside typically consists of a nitrogenous base and a sugar. In naturally occurring DNA, the sugar group is typically β-D-2'-deoxyribofuranose and the nitrogenous base is typically a purine (e.g., adenine, A, and guanine, G) or a pyrimidine (e.g., thymine, T, or cytosine, C). Most commonly, the C-1 carbon of the D-2'-deoxyribose is attached to the N-1 of a pyrimidine or the N-9 of a purine; the configuration of this N-glycosidic linkage is β (the base lies above the plane of the sugar). The four naturally occurring deoxyribonucleosides are called deoxyadenosine (dA), deoxyguanosine (dG), deoxythymidine (dT), and deoxycytidine (dC). Deoxynucleotides are phosphate esters of deoxynucleosides. Most commonly, the phosphate ester is formed at the 5'—OH group of the sugar group (i.e., the 5'—OH is converted to 5'—$OPO_3^{-2}$); the resulting compound is referred to as a nucleoside 5'-phosphate or a 5'-nucleotide. More than one phosphate group may be attached (e.g., diphosphate, 5'—$OPO_2OPO_3^{-3}$; triphosphate, 5'—$OPO_2OPO_2PO_3^{-4}$). For example, an important activated precursor in the synthesis of DNA is deoxyadenosine 5'-triphosphate (dATP).

As mentioned above, DNA is a polymer of deoxyribonucleotide units. Most commonly, the polymeric backbone of DNA is constant and consists of deoxyribose groups linked by phosphate groups; more specifically, the 3'-position of one deoxyribose group (it was 3'—OH) is linked to the 5'-position of the adjacent deoxyribose group (it was 5'—OH) via a phosphodiester group (i.e., —OP(=O)($O^-$)O—). The variable aspect of DNA is its sequence of bases (e.g., A, G, C, and T) attached at the 1'-position of each deoxyribose group. Thus, the four repeating units (often referred to as residues) most commonly found in DNA are referred to as deoxyadenylate, deoxyguanylate, deoxycytidylate, and deoxythymidylate.

A DNA polymer may be conveniently be represented by its component bases, often referred to as its "sequence." Since one end of the DNA molecule terminates in a sugar group having a free 3'-group (e.g., 3'—OH, 3'—$OPO_3^{-2}$) and the other end terminates with a sugar group having a free a 5'-group (e.g., 5'—OH, 5'—$OPO_3^{-2}$), it is necessary to unambiguously identify which end is which. As a matter of universal convention, DNA is recited left to right, from the 5'-terminus to the 3'-terminus. Thus, ACG denotes 5'—ACG-3' or 5'—A-3'-5'-C-3'-5'-G-3'. In some cases, a DNA polymer may be cyclic and thus have no terminus; in such cases, the sequence is recited from 5' to 3', from a suitable, possibly arbitrary, starting point.

DNA usually occurs in a double-helix form (Watson-Crick), wherein two helical polynucleotide chains (e.g., strands) are coiled around a common axis, with each chain running in opposite directions ("anti-parallel") with respect to their 5'-3' polarity, as discussed above. The purine and pyrimidine bases are on the inside of the helix, whereas the phosphate and deoxyribose groups are on the outside. The planes of the bases are roughly perpendicular to the helix axis and the planes of the sugars are nearly parallel to the helix axis. The diameter of the helix is about 20 Å. Adjacent bases are separated by about 3.4 Å along the helix axis and are related by a rotation of about 36°. Thus, the helical structure repeats after ten residues on each chain, that is, at intervals of 34 Å. A relatively small DNA helix wherein each strand has 1000 residues is approximately 3.4 μm from end-to-end.

The two chains are held together by hydrogen bonding between pairs of bases (often referred to as "base pairs") and by stacking interaction (π-electron sharing) between adjacent base pairs. Because of steric and hydrogen bonding reasons, a purine is always paired with a pyrimidine; more specifically, adenine is always paired with thymine (via two hydrogen bonds), and guanine is always paired with cytosine (via three hydrogen bonds). Thus, each base pair contributes about 620 daltons to the molecular weight of the double helix. Note, however, that there is no restriction on the sequence of bases along the polynucleotide chain. It is the precise sequence of bases that carries genetic information.

The two strands of a DNA double helix readily come apart when the hydrogen bonds between its paired bases are disrupted, as may be accomplished by heating a solution of DNA or by adding acid or alkali to ionize the bases. The resulting unwinding of the double helix is commonly referred to as "melting" or "denaturation," and is characterized by a melting temperature at which half of the molecules are rendered single stranded. Melting is usually reversible, and the unwound chains may come together to reform the helix, in a process commonly referred to as "annealing," "renaturation," or "hybridization."

Ribonucleic acid (RNA) is another example of a polynucleotide. Like DNA, RNA is a polymer consisting of nucleotides jointed by a 3'-5' phosphodiester bonds. The covalent structure of RNA differs from that of DNA in two important respects. In RNA, the sugar group is β-D-ribose (instead of β-D-2'-deoxyribose). Also, one of the four major bases in RNA is the pyrimidine uracil, U (which replaces thymine found in DNA). Thus, in RNA, base pairs are AU and GC (instead of AT and GC found in DNA). RNA can be single-stranded or double-stranded, though usually it is single stranded. Although RNA cannot form a double helix of the B-DNA type, RNA often forms regions of double-helical structure produced by self-hybridization and the formation of hairpin loops.

DNA may be replicated with the aid of an enzyme, referred to as a DNA polymerase (e.g., DNA pol α,β,γ,δ,ε). Typically, a DNA polymerase catalyzes the step-by-step addition of deoxyribonucleotides units to the 3'-terminus of a pre-existing DNA chain (often referred to as a primer) according to a template (typically a single strand of DNA) to which the primer has been hybridized. Typically, the chain-elongation reaction catalyzed by DNA polymerase is a nucleophilic attack of the 3'—OH terminus of the primer on the innermost (i.e., α- phosphorus) phosphorus atom of a deoxyribonucleoside triphosphate; a phosphodiester bridge is formed and pyrophosphate concomitantly released. The DNA polymerase catalyzes the formation of the phosphodiester bond only if the base on the incoming nucleotide is complementary to the base on the template strand; indeed, mismatched base pairs are removed. In this way, the template driven replication proceeds with very high fidelity and with an error rate of less than $10^{-8}$ per base pair.

Genes comprise DNA. A particular DNA sequence encodes a particular amino acid sequence. In this way, proteins (poly amino acids, polypeptides) are encoded by DNA. DNA, preferably double stranded DNA, is used as a template for an RNA polymerase (e.g, RNA pol I, II, III) to produce messenger RNA (mRNA) which encodes a particular protein. In this way, DNA is transcribed into mRNA. Triplets of mRNA residues, referred to as "codons," represent each of the 20 naturally occurring amino acids according to the genetic code. The mRNA is then itself used as a template and is "threaded" through a ribosome (comprised of ribosomal RNA, rRNA, and ribosomal proteins) to produce the protein encoded by the particular mRNA. In this way, mRNA is translated into protein. Individual amino acids, which are attached to a short piece of transfer RNA (tRNA) which also recognizes a specific codon in the mRNA, are incorporated into the growing protein by the ribosome. Coded DNA (cDNA) may be obtained from mRNA (acting as a template) using the enzyme reverse transcriptase. In this way, coding a particular protein may be obtained in a DNA form which is often more suitable for cloning and other genetic manipulations.

Polymerase chain reaction (PCR), developed in the mid-1980's, permits the simple and rapid production of large quantities of a specified DNA sequence without resorting to cloning. PCR exploits the ability of DNA polymerases (e.g., Taq polymerase) to replicate DNA from a single stranded template DNA. Both DNA strands can serve as templates; single stranded templates may be easily produced, for example, by heating double-stranded DNA to a temperature near boiling. PCR requires that certain reagents be present in the reaction mixture, including activated nucleotide monomers (e.g., ATP, GTP, CTP, TTP) and $Mg^{+2}$. PCR also requires a small piece of double stranded DNA at which to initiate (i.e., prime) replication, which is usually provided by annealing (hybridizing) a suitable oligonucleotide "primer" at the site from which replication is to begin. Since DNA polymerase replicates DNA in the 3' to 5' direction, both strands may act as templates if two primers are provided, one which will hybridize to one strand, and one which will hybridize to the other strand. Following replication, the newly grown double stranded DNA (comprising the template strand and newly grown strand) is melted (e.g., by heating to near boiling), and each of the resulting single strands may act as a template in the next cycle. In this way, each cycle effectively doubles the number of desired single-stranded DNA fragments, and increases the proportion of DNA fragments which are identical (as defined by the positions of the two primers).

PCR is readily adapted to automation. Typically, a DNA sample is initially heated (e.g., 94° C., 5 min) to separate the strands, and the reagents (e.g., Taq polymerase, primers, excess activated nucleotide monomers, $Mg^{+2}$, etc.). In a first heating step (e.g., 30-65° C., 30 s), primers bind to the DNA strands. In a second heating step (e.g., 65-75° C., 2-5 min), the polymerase synthesizes new DNA strands. In a third heating step (e.g., 94° C., 30 s), the strands of the resulting double stranded DNA are separated. The three steps are repeated for each cycle. Typically, from 10-60 cycles are performed. Theoretically, 32 cycles will yield approximately $10^9$ copies of the desired double stranded DNA fragment.

Specific oligonucleotides (e.g., DNA, RNA) may often be synthesized directly from monomers, dimers, etc. without the aid of a polymerase and without the need for a template strand. Typically, a solid-phase method is employed in which nucleotides are added to a nascent oligonucleotide which is attached to a solid support. A number of solid-phase oligonucleotide syntheses are known, including triester, phosphite, and phosphoramidate methods, though the last is often the preferred.

Typically, solid-phase oligonucleotide synthesis by the phosphoramidate method involves stepwise synthesis of the oligonucleotide in the 5'-direction by reiteratively performing four steps: deprotection, coupling, capping, and oxidation. In the first step ("deprotection"), the growing oligonucleotide, which is attached at the 3'-end via a 3'—O-group to a solid support, is 5'-deprotected to provide a reactive group (i.e., a 5'—OH group). In the second step ("coupling"), the 5'-deprotected supported oligonucleotide is reacted with the desired nucleotide monomer, which itself has first been converted to a 5'-protected, 3'-phosphoramidite. For example, the 5'—OH group may be protected in the form of a 5'—ODMT group (where DMT is 4,4'-dimethoxytrityl) and the 3'—OH group may converted to a 3'-phosphoramidite, such as —OP(OR')$NR_2$, where R is the isopropyl group, —CH($CH_3$)$_2$, and R' is, for example, —H (yielding a phosphoramidite diester), or —$CH_3$, —$CH_2CH_3$, or the beta-cyanoethyl group, —$CH_2CH_2CN$ (yielding a phosphoramidite triester). The 3'-phosphoramidite group of the monomer reacts with the deprotected 5'—OH group of growing oligonucleotide to yield the phosphite linkage 5'—OP(OR')O-3'. Not all of the growing oligonucleotides will couple with the provided monomer; those which have not "grown" would yield incomplete oligonucleotides and therefore must be withdrawn from further synthesis. This is achieved by the third step ("capping"), in which all remaining —OH groups (i.e., unreacted 5'—OH groups) are capped, for example, in the form of acetates (5'—OC(O)$CH_3$) by reaction with acetic anhydride. Finally, in the oxidation step, the newly formed phosphite group (i.e., 5'—OP(OR')O-3') of the growing oligonucleotide is converted to a phosphate group (i.e., 5'—OP(=O)(OR')O-3'), for example, by reaction with aqueous iodine and pyridine. The four-step process may then be reiterated, since the oligonucleotide obtained after oxidation remains 5'-protected and is ready for use in the first deprotection step described above. When the desired oligonucleotide has been obtained, it may be cleaved from the solid support, for example, by treatment with alkali and heat. This step may also serve to convert phosphate triesters (i.e., when R' is not —H) to the phosphate diesters (—OP(=O)$_2$O—), as well as deprotect base-labile protected amino groups of the nucleotide bases.

Most methods for detecting specific DNA and RNA sequences rely on nucleic acid hybridization. Typically, such methods rely on the formation of a duplex between a target DNA or RNA sequence and a labeled nucleic acid hybridization probe. Hybridization probes are usually complementary to a specific part of the target nucleic acid. Note, however, that a hybridization probe may be only partially complementary, yet still form a stable duplex with the target sequence. Typically, hybridization probes are at least 70% complementary, though more often at least 90% complementary to the target sequence. Hybridization probes usually have a sequence which is long enough to ensure both selective and stable hybridization. Typically, hybridization probes have from 6 to about 500 monomer units (e.g., nucleotides), though more typically from about 10 to about 100 monomer units. Specific hybridization probes having the desired sequence are often synthesized directly using solid-phase oligonucleotide synthesis methods. Labeled nucleic acid probes are utilized in a variety of assay formats including dot blots, Southern blots (DNA target), Northern blots (RNA target), in situ hybridization, plaque hybridization, and colony hybridization. A number of different substances have been used to label a nucleic acid probe, and a number of different methods have been used to detect these labels. See, for example, Kricka, 1992.

In one embodiment, the assays of the present invention may be employed to detect DNA by employing two oligonucleotide hybridization probes, one with an attached ECL label and the other with an attached ECL quenching moiety. The probes may be specifically chosen so that, upon annealing with the target DNA, the ECL label and ECL quenching moiety are brought into quenching contact, thereby reducing the observed ECL emission. Thus, a decrease in ECL emission may be correlated with the amount of target DNA present in the sample.

In another embodiment, the assays of the present invention may be employed to detect DNA by employing a oligonucleotide hybridization probe which possesses both an ECL label and an ECL quenching moiety, in combination with a DNA polymerase (typically in a non-separation assay). For example, a target DNA in a sample may be detected by forming a mixture comprising the sample, a suitable oligonucleotide hybridization probe having both an ECL label (L) and an ECL quenching moiety (Q), a suitable oligonucleotide primer which hybridizes to the target DNA at a position upstream from the hybridization probe, a 5'-specific DNA exo-polymerase, such as the well known Taq polymerase (derived from Thermus Aquaticus), and suitable concentrations of activated nucleotide monomers (e.g., ATP, GTP, CTP, TTP) and other reagents (e.g., KCl, Tris HCl, $MgCl_2$). Typically, the ECL label and ECL quenching moiety of the unhybridized oligonucleotide hybridization probe are in quenching contact, and low ECL emission is observed. The mixture is processed to permit the hybridization probe and primer to anneal to the target DNA. Typically, the ECL label and ECL quenching moiety of the hybridized probe are in quenching contact, and, again, low ECL emission is observed. The polymerase reaction is then allowed to proceed. Starting at the 3'-end of the primer, the 5'-specific DNA exo-polymerase extends the primer in the 5'-direction, one nucleotide at a time, using the target DNA as a template. If, as the polymerase proceeds downstream in the 5'-direction, it encounters a bound hybridization probe, the polymerase will degrade the bound probe as it extends the primer. The hybridization probe is converted to short oligonucleotide fragments (typically monomers), which are freed from the target DNA and enter the solution mixture. Since the ECL label and the ECL quenching moiety were attached to different monomer units, they are, upon degradation, freed into solution and thus are no longer held in quenching contact. Thus, an increase in ECL emission may be correlated with the amount of target DNA present in the sample. An analogous method has been illustrated for fluorescence labels and fluorescence quenchers. See, for example, Wittwer, 1997.

In yet another embodiment, the assays of the present invention may be employed to detect DNA by employing a oligonucleotide hybridization probe which possesses both an ECL label and an ECL quenching moiety, and which has self-hybridization sequences. In the absence of the target DNA, the probe self-hybridizes (typically forming a hairpin or hairpin-loop structure), bringing the ECL label and the ECL quenching moiety into quenching contact. In the presence of the target DNA, the probe preferentially anneals to the target DNA, and in doing so, separates the ECL label from the ECL quenching moiety so that they are no longer in quenching contact, and the ECL emission increases. Thus, an increase in ECL emission may be correlated with the amount of target DNA present in the sample.

In one embodiment, the assays of the present invention may be employed as immunoassay to detect antibodies or antigens. Antibodies, also referred to as immunoglobulins, are proteins synthesized by an animal in response to the presence of a foreign substance. They are secreted by plasma cells, which are derived from B lymphocytes (B cells). These soluble proteins are the recognition elements of the humoral immune response. Each antibody has a specific affinity for the foreign material that stimulated its synthesis, and readily binds with the foreign material to form a complex. A foreign macromolecule capable of eliciting antibody formation is called an antigen (or immunogen). Proteins, polysaccharides, and nucleic acids are usually effective antigens. The specific affinity of an antibody is not for the entire macromolecular antigen, but instead for a particular site on the antigen called the antigenic determinant (or epitope). Most small molecules do not stimulate antibody formation. However, they can elicit the formation of specific antibodies if they are attached to macromolecules. The macromolecule is then the carrier of the attached chemical group, which is called a haptenic determinant. The small foreign molecule by itself is called a hapten. Antibodies elicited by attached haptens will bind unattached haptens as well.

Structurally, antibodies consist of four individual protein chains: two light (L) chains of molecular weight about 17,000 daltons, and two heavy (H) chains of molecular weight about 35,000, which are held together by disulfide bonds. In humans, there are five classes of heavy chains, $\mu, \delta, \gamma, \epsilon$, and $\alpha$, and two classes of light chains, $\kappa$ and $\lambda$. It is the class of heavy chain which characterizes the antibody (i.e., immunoglobulin, Ig) as an IgM, IgD, IgG, IgE, or IgA, respectively. Generally, each of the light and heavy chains consist of a variable region (at the amino end) and a constant region (at the carboxy end), though the heavy chain's constant region is often sub-divided into domains. Usually, it is the amino acid sequence of the variable regions of the light and heavy chains which determine the specificity of antigen binding; thus each antibody usually has two antigen binding sites. Generally, antibodies may also be structurally described according to their products upon enzymatic degradation, for example, by papain, pepsin, or trypsin. Typically, upon digestion by the enzyme papain, two Fab fragments (each having one complete light chain and part of one heavy chain; each has one antigen binding site) and one Fc fragment (having the remainder of each of the two heavy chains, and having no antigen binding sites) are obtained. Typically, upon digestion by the enzyme pepsin, one $F(ab')_2$ fragment (having two complete light chains and one part of each heavy chain; has two antigen binding sites) and one pFc' fragment (having the remainder of each of the two heavy chains, and having no antigen binding sites) are obtained.

Each antibody-producing cell produces only one type of antibody, and the specific type of antibody produced by a given cell is related to that cell's initial interaction with the antigen. In this way, when a foreign substance is introduced into an animal, a large number of different antibodies are produced, with varying binding specificity for the antigen. B lymphocytes, the precursors of plasma cells, are triggered to divide and proliferate by the binding of antigen to receptors, antibody molecules which span the membrane and are have binding sites exposed on the cell surface. The soluble antibodies subsequently produced by the activated cell have the same specificity as the membrane-bound antibody.

Antibodies may be generated, for example, by administering an antigen to an animal. Typically, the antigen comprises a hapten bound to a hapten determinant (e.g., a carrier macromolecule), such as serum albumin, serum globulins, lipoproteins, and the like. The antigen may be conveniently prepared for injection by rehydrating lyophilized antigen to form a solution or suspension, and is usually mixed with an adjuvant. Examples of adjuvants include water-in-oil emulsions, such as Freund's complete adjuvant for the first administration, and Freund's incomplete adjuvant for booster doses. Typically, the antigen composition is administered at a variety of sites, and in two or more doses over a course of at least about 4 weeks.

Serum (i.e., polyclonal antiserum) is harvested from the animal and tested for the presence of desired antibody using the antigen or an antigen analog in a standard immunoassay or precipitation reaction. The polyclonal antiserum will typically contain some antibodies which are not reactive with the antigen, and some which are reactive with the antigen but are also cross-reactive with other antigens (e.g., not highly selective). Methods for purifying specific antibodies from a polyclonal antiserum are known in the art. A particularly effective method is known as affinity purification which employs a column having antigen conjugated to a solid phase (e.g., a Sepharose column). The polyclonal antisera is passed over the column, the column washed, and the desired antibody eluted with a mild denaturing buffer. For general techniques used in raising, purifying and modifying antibodies, and the design and execution of immunoassays, see, for example, Weir et al., 1996; Coligan et al., 1991; Wild, 1994; and Masseyeff et al., 1993.

Since a given antibody-producing cell (e.g., a splenocyte) produces only one specific antibody, it is usually necessary to clone that cell in order to generate quantities of that specific antibody, for example, by fusing the antibody-producing cell with a non-antibody producing myeloma cell (a cell produced by multiple myeloma, a malignant disorder of antibody-producing cells). Fusion may be achieved, for example, by exposing the cells to polyethylene glycol, but more usually achieved by transfection with Epstein Barr Virus, or transformation with oncogenic DNA.

Unlike the antibody producing cell, the fused cell retains the neoplastic character of the myeloma cell, and thus proliferates in culture; in this way, the antibody-producing cell is immortalized. Typically, many antibody-producing cells are cloned and cultured, and those clones that produce antibodies of the of the desired specificity are selected. Specificity is typically determined from culture supernatants, for example, by the antigen as the detecting reagent in an immunoassay. A supply of the desired monoclonal antibody from the selected clone can then be purified from a large volume of culture supernatant, or from the ascites fluid of suitably prepared host animals injected with the clone. The antibody may optionally be purified using standard biochemical preparation techniques such as ammonium sulfate precipitation, ion exchange chromatography, and gel filtration chromatography. In another method, antibody-producing cells may be harvested from an immunized animal donor, or they can be harvested from an unimmunized donor and pre-stimulated in vitro by culturing in the presence of antigen and immunostimulatory growth factors. Cells which produce antibody of the desired specificity can be selected by contacting with antigen under conditions which result in proliferation of specific clones but not non-specific clones. For general techniques pertaining to monoclonal antibodies and hybridomas, see, for example, Harrow & Lane, 1988; Wands et al., 1985; Milstein et al., 1984; and Hoffmann, 1984.

Thus, the term "antibody," as used herein, relates to both polyclonal and monoclonal antibody, and encompasses not only intact antibody molecules, but also such antibody fragments and antibody derivatives (as may be prepared by techniques known in the art) which retain the antibody activity of an intact immunoglobulin. In this context, "antibody activity" relates to the ability of an antibody to bind a specific antigen in preference to other potential antigens via the antibody's antigen binding site. Fragments and other derivatives of antibodies can be prepared by methods of standard protein chemistry, such as subjecting the antibody to cleavage with a proteolytic enzyme like pepsin, papain, or trypsin; and reducing disulfide bonds with such reagents as dithiothreitol. Genetically engineered variants of intact antibodies can be produced by obtaining a polynucleotide encoding the antibody, and applying the general methods of molecular biology to splice encoding sequences or introduce mutations and translate the variant. Antibodies that are engineered variants of particular interest include chimeric and humanized antibodies, Fab-like fragments, single-chain variable region fragments (scFv), and diabodies.

Although antibodies are usually screened or purified according to their ability to react with the antigen, they are often also screened according to other criteria, such as low cross-reactivity with potential interfering substances; antibody-antigen reaction rates and antibody-antigen affinity, both of which may affect the sensitivity and capacity of the antibody-antigen system; and the titer of antibody produced by a biological source. Ultimate selection of an antibody may require a compromise between these various features.

In one embodiment, the assays of the present invention may be employed as immunoassay to detect an antibody or an antigen. For example, a target antibody (to be detected) in a sample may first be derivatized to possess one or more ECL quenching moieties (using, for example, quenching agents with amino-reactive groups). An antigen or antigen analog may then be prepared which possesses an ECL label. Upon mixing, antibody-antigen complexes are formed wherein the ECL label and the ECL quenching moiety are brought into quenching contact, thereby reducing the observed ECL emission. Thus, a decrease in ECL emission may be correlated with the amount of target antibody present in the sample. Alternatively, target antibodies may be derivatized to possess ECL labels, and the antigen or antigen analog may be prepared to possess ECL quenching moieties. Analogous methods may be used to detect target antigens.

In another embodiment, the assays of the present invention may be employed as a competition immunoassay to detect an antibody or an antigen. For example, a target antibody (to be detected) in a sample may first be derivatized to possess one or more ECL quenching moieties (using, for example, quenching agents with amino-reactive groups). An antigen or antigen analog may then be prepared which possesses an ECL label. Upon mixing, antibody-antigen complexes are formed wherein the ECL label and the ECL quenching moiety are brought into quenching contact, thereby reducing the observed ECL emission. A second antigen or antigen analog, which lacks an ECL label, and which has a similar binding affinity for the target antibody may be added. (Alternatively, the first antigen may be unlabeled and the second antigen may be labeled.) In this way, the unlabeled antigen competes with the labeled antigen; labeled antigen which is freed upon competition will increase the ECL emission. Thus, a change in ECL emission may be correlated with the amount of target antibody present in the sample. Analogous methods may be used to detect target antigens.

In one embodiment, the assays of the present invention may be employed to detect enzymes, enzyme agonists, and enzyme antagonists. Enzymes, the great majority of which are proteins (poly amino acids), are catalysts of biological systems. Enzymes typically offer substantial catalytic power (often accelerating reactions by a factor of $10^6$ or more) and exquisite selectivity. By utilizing a full repertoire of intramolecular and intermolecular forces, enzymes are able both to bring substrates into optimal orientation for making and breaking chemical bonds, and to stabilize the transition states for the desired reaction path. An enzyme usually catalyzes a single chemical reaction or a set of closely related reactions, with a very low proportion of side-reactions which yield undesired by-products, and with a very high degree of selectivity (often virtually absolute).

The first step in enzymatic catalysis involves the formation of an enzyme-substrate complex, wherein the substrate is typically bound to a specific region of the enzyme usually referred to as the active site. The active site typically occupies a relatively small portion of the total volume of an enzyme, and many of the amino acid residues in an enzyme are not in contact with the substrate. The active site is a three-dimensional entity, typically formed by chemicals groups on different amino acid residues (often far apart in a linear amino acid sequence) that come together as a result of the enzymes primary, secondary, tertiary, and quaternary structure. Typically, substrates are bound to enzymes by multiple weak attractions (e.g., electrostatic bonds, hydrogen bonds, van der Waals forces, hydrophobic interactions). In most cases, the active site is a crevice or cleft in the enzyme, into which a complementary substrate is bound. The specificity of binding typically depends on the arrangement of atoms in the active site. For example, the enzyme and substrate may be represented metaphorically by a lock and key, respectively, which have complementary structures. Alternatively, the enzyme and substrate may have complementary structures only after formation of an enzyme-substrate complex.

The activity of enzymes may often be increased or decreased by certain small molecules and ions (e.g., drugs, toxins). Enzyme inhibitors typically reduce enzyme activity. An inhibitor may bind irreversibly at the active site, in which case the enzyme is rendered essentially permanently inactive. Alternatively, an inhibitor may bind reversibly at the active site, in which case the inhibitor, referred to as a competitive inhibitor, prevents the substrate from binding and competes with substrate for the binding site. Also, an inhibitor (typically referred to as a noncompetitive inhibitor or antagonist) may bind at a site other than the active site, and thereby reduce the enzyme's ability to bind substrate at the binding site. In contrast, molecules which increase enzyme activity (often referred to as agonists) typically bind at a site other than the active site, and thereby increase the enzyme's activity.

In one embodiment, the assays of the present invention may be employed to detect (or identify) an enzyme, substrate, irreversible inhibitor, competitive inhibitor, antagonist, or agonist. For example, an enzyme (to be detected) in a sample may first be derivatized to possess one or more ECL quenching moieties (using, for example, quenching agents with amino-reactive groups). An enzyme substrate may then be prepared which possesses an ECL label. Upon mixing, enzyme-substrate complexes are formed wherein the ECL label and one or more ECL quenching moieties are brought into quenching contact, thereby reducing the observed ECL emission. Thus, a decrease in ECL emission may be correlated with the amount of target enzyme present in the sample. Alternatively, target substrates may be derivatized to possess ECL labels, and the enzyme may be prepared to possess ECL quenching moieties. Analogous methods may be used to detect target substrates, substrate analogs, irreversible inhibitors, competitive inhibitors, antagonists, and agonists.

In another embodiment, the assays of the present invention may be employed as a competition assay to detect, for example, an enzyme, substrate, substrate analog, competitive inhibitor, antagonist, or agonist. For example, to detect a substrate in a sample, one may first derivatize a suitable enzyme to possess one or more ECL quenching moieties (using, for example, quenching agents with amino-reactive groups). A substrate analog, which has a similar binding affinity for the enzyme as the substrate, and which possesses an ECL label, may then be prepared. Upon mixing the enzyme and substrate analog, enzyme-substrate analog complexes are formed wherein the ECL label and one or more ECL quenching moieties are brought into quenching contact. The sample, containing the substrate to be detected, is then added. The substrate, which lacks an BCL label, competes with the labeled substrate analog; labeled substrate analog which is freed upon competition will increase the ECL emission. Thus, an increase in ECL emission may be correlated with the amount of target substrate present in the sample. Analogous methods may be used to detect enzymes, substrate analogs, competitive inhibitors, antagonists, and agonists.

In one embodiment, the assays of the present invention may be employed to detect materials which may be selectively derivatized to possess one member of a strong binding pair. Examples of strong binding pairs include biotin-avidin and biotin-avidin analogs, such as biotin-streptavidin. Biotin, also known as vitamin H of the vitamin B complex, is an imidazole pentanoic acid of empirical formula $C_{10}H_{15}O_3N_2S$. Avidin, a 70 kilodalton protein found in egg white, has a very high binding affinity for biotin. Streptavidin, a similar protein found in the bacteria, *Streptomyces avidinii*, has an even higher binding affinity for biotin, partially due to its four biotin binding sites.

For example, a target molecule (to be detected) may be selectively derivatized to possess both a biotin moiety (using, for example, a commercially available biotinylating agent) and an ECL label. A streptavidin derivative may be prepared which possesses one or more quenching moieties. Upon mixing, biotin-streptavidin complexes are formed wherein the ECL label and one or more ECL quenching moieties are brought into quenching contact, thereby reducing the observed ECL emission. Thus, a decrease in ECL emission may be correlated with the amount of target molecule present in the sample. Alternatively, the target molecule may be selectively derivatized to possess, for example, biotin/ECL quenching moiety, avidin/ECL label, or avidin/ECL quenching moiety; counterparts reagents would then comprise avidin/ECL label, biotin/ECL quenching moiety, and biotin/ECL label, respectively.

The present invention also provides reagents, reagent sets comprising one or more reagents, and reagent kits comprising one or more reagent sets, for use in the assay methods of the present invention. Reagents may be in solid, liquid, or gaseous form, though typically are in solid or liquid form. Examples of reagents include, but are not limited to, reagents for ECL labeling, reagents for attaching ECL quenching moieties, electrolyte compositions, solvents, and buffers. Reagents and/or sets of reagents for use in the assays of the present invention are typically provided in one or more suitable containers or devices. Reagent sets are typically presented in a commercially packaged form, as a composition or admixture where the computability of reagents will allow, as a reagent kit; for example, as a packaged combination of one or more containers, devices, or the like holding one or more reagents, and usually including written instructions for the performance of the assays.

D. Methods for Measuring ECL

A range of suitable apparati for measuring the ECL of sample are known in the art. See, for example, Blackburn et al., 1991; Leland et al., 1990; Hall et al., 1991. Typically, ECL is measured using an apparatus which comprises (i) a receptacle for the sample (which is typically a liquid); (ii) two or more electrodes disposed in the receptacle and in contact with the composition to be examined, one of which is the "working electrode" at which electrochemiluminescent species are produced, and (iii) a detector, which detects some fraction of the photons emitted during electrochemiluminescence.

For convenience, the ECL apparatus typically has three electrodes: a working electrode, a counter electrode, and a reference electrode. Often the reference electrode (e.g., a standard Ag/AgCl electrode) is located some distance from, but in contact (via the electrolyte) with, the working and counter electrodes. The working and counter electrodes are typically noble or relatively inert metals such as platinum and gold.

The detector may be any device which detects (and preferably quantifies) photons, such as a photomultiplier tube (PMT), a photodiode, a charge coupled device, photographic or light sensitive film or emulsion. Typically, the detector is a PMT, which may be chosen to be particularly sensitive for a certain range of photons, for example, ultraviolet, visible, or infrared. The detector is typically positioned in a manner so that it may readily and efficiently detect the photons emitted during ECL. For example, in one embodiment, the working electrode is a gold or platinum disk, the PMT detector is positioned directly across from the front flat surface of the working electrode, and the composition to be examined flows laterally over the disk, between the disk and the PMT detector.

For convenience, the ECL apparatus typically incorporates means for fluid handling, including, for example, inlets to and outlets from the sample receptacle which are connected to reservoirs (e.g., via tubing) for reagents, electrolyte/buffers, and the sample composition, and pumps (e.g., a peristaltic pump) for moving liquids between the receptacle and the reservoirs. In this way, the apparatus may be used to measure ECL in either a static or flow-through configuration.

A well known and commercially available ECL apparatus is the Origen I Analyzer®, which integrates a photometer (as detector), an electrochemical cell (receptacle and electrodes), a potentiostat (for operating the electrochemical cell), and means for fluid and sample handling. The analyzer employs a flow injection system that permits rapid and reproducible determinations of sequential samples. The photometer is a photomultiplier tube (typically red-sensitive for optimal detection of $Ru(bpy)_3^{2+}$ labels) positioned directly above the working electrode so that the light from the electrode is recorded and integrated during each measurement.

As discussed above, ECL is the emission of photons of electromagnetic radiation (e.g., light) from an electronically excited chemical species which has been generated electrochemically. Thus, to measure the ECL of a particular sample, the sample must be electrolyzed to produce electro-oxidized and/or electro-reduced species which, either directly and following further reaction, emit photons. The sample is typically electrolyzed by applying an electrical potential to the working electrode, for example, with a battery or other source of electromotive force (EMF). For convenience, the potential difference is reported as the potential of the working with respect to the reference electrode, with electrochemical current (faradaic current) flowing between the working and auxilliary electrodes. Thus, the working electrode potential typical ranges from −10.00 to +10.00 V, though more commonly from −6.00 to +6.00 V, and even more commonly from −3.00 to +3.00 V. The working electrode potential may be static, may alternate, or may reflect a more complex function. Means for applying a particular electric potential (e.g., waveform) are well known in the electrochemical arts. See, for example, Kamin et al., 1992. The potential which must be applied to the working electrode in order to produce ECL is a function of the exact chemical species which are involved in the ECL reaction sequence as well as other factors such as the pH of the sample composition and nature of the electrode. It is well known to those of skill in the art of ECL how to determine both the optimal potential to produce ECL as well as the optimum wavelength at which to detect the ECL.

Again, in order to measure the ECL of a particular sample, the sample must be electrolyzed to produce electro-oxidized and/or electro-reduced species which, either directly or following further reaction, emit photons. To effect optimum electrolysis, ions should be present in the sample composition which may migrate between the working electrode and the counter electrode, thereby effecting the transfer of charge. Therefore, in order to facilitate the ECL measurement, the sample is typically mixed with an ECL assay media (e.g., ECL assay buffer) which comprises ions which will effect the transfer of charge during the ECL measurement but will not interfere with the ECL reaction sequence.

The term "ECL assay media," as used herein, pertains to a composition which is optionally (though usually) mixed with the sample prior to performing the ECL measurement. Generally, the ECL assay media is a fluid, though more typically is a liquid, and comprises one or more dissolved salts. Typically, the ECL assay is a liquid and comprises one or more solvents and one or more dissolved salts. Typically, the salts are present in millimolar concentrations.

In one embodiment, the ECL assay comprises water (i.e., $H_2O$) and one or more dissolved salts. Examples of water soluble salts include chloride salts such as NaCl, KCl, $N(C_4H_9)_4Cl$; bromide salts such as NaBr, KBr, $N(C_4H_9)_4Br$; nitrate salts such as $KNO_3$, $NaNO_3$, and $N(C_4H_9)_4NO_3$; phosphate salts such as $Na_3PO_4$, $K_3PO_4$, $Na_2HPO_4$, $K_2HPO_4$, $NaH_2PO_4$, and $KH_2PO_4$; and sulfate salts such as $Na_2SO_4$, and $K_2SO_4$.

In another embodiment, the ECL assay comprises one or more organic solvents and one or more dissolved salts. Examples of suitable organic solvents include acetonitrile (i.e., $CH_3CN$, ACN), dimethylsulfoxide (i.e., $(CH_3)_2SO$, DMSO), N,N-dimethylformamide (i.e., $(CH_3)_2NCHO$, DMF), methanol (i.e., $CH_3OH$), and ethanol (i.e., $C_2H_5OH$). Examples of salts which are soluble in typical organic solvents include tetrabutylammonium salts, such as tetrabutylammonium tetrafluoroborate (i.e., $(C_4H_9)_4NBF_4$).

In some embodiments, and particularly in those wherein the ECL assay media comprises water, the ECL assay media is pH buffered. For example, an aqueous ECL assay media may conveniently be pH buffered by the addition of a phosphate (e.g., $KH_2PO_4$, typically at about 0.01 to 0.05 M) followed by adjusting the pH to a desired value (e.g., physiological pH 7.2) by the addition an appropriate amount of a suitable strong acid (e.g., HCl) or strong base (e.g., NaOH). Once buffered, the pH of the ECL assay media is relatively insensitive to small changes in its chemical composition, such as those which may occur during the ECL measurement.

The ECL assay media may also comprise one or more ECL coreactants, which take part in the chemical reactions involving the electro-oxidized and/or electro-reduced species, the final result being the emission of a photon (i.e., ECL). The term "ECL coreactant," or more simply "coreactant," as used herein, pertains to a chemical compound which, either itself or its electrochemical reduction/oxidation product(s), plays a role in the ECL reaction sequence. Often coreactants permit the use of simpler means for generating ECL (e.g., the use of only half of the double-step oxidation-reduction cycle) and/or improved ECL intensity. In one embodiment, coreactants are chemical compounds which, upon electrochemical oxidation/reduction, yield, either directly or upon further reaction, strong oxidizing or reducing species in solution. An example of a coreactant is peroxodisulfate (i.e., $S_2O_8^{2-}$, persulfate) which is irreversibly electro-reduced to form oxidizing $SO_4^{*-}$ ions. Another example of a coreactant is oxalate (i.e., $C_2O_4^{2-}$) which is irreversibly electro-oxidized to form reducing $CO_2^{*-}$ ions. An example of a class of coreactants which act as reducing agents are amines or compounds containing amine groups, including, for example, tri-n-propylamine (i.e., $N(CH_2CH_2CH_3)_3$, TPAH).

Examples of coreactants include, but are not limited to, lincomycin; clindamycin-2-phosphate; sparteine; erythromycin; 1-methylpyrrolidone; N-ethylmorpholine; diphenidol; atropine; trazodone; 1-ethylpiperidine; hydroflumethiadize; hydrochlorothiazide; clindamycin; tetracyline; streptomycin; gentamycin; reserpine; trimethylamine; tri-n-butylamine; triethanolamine; piperidine; 1,4-piperazine bis(ethanesulfonic acid); tri-n-butylphosphine; N,N-dimethylaniline; pheniramine; bromopheniramine; chloropheniramine; diphenylhydramine; di-n-propylamine; 2-dimethylaminopyridine; pyrilamine; 2-benzylaminopyridine; leucine; valine; glutamic acid; phenylalanine; alanine; arginine; histidine; cysteine; tryptophan; tyrosine; hydroxyproline; asparagine; methionine; theonine; serine; cyclothiazine; trichloromethiazide; 1,3-diaminopropane; piperazine, chlorothiazide; hydrozinothalanzine; barbituric acid; persulfate; nicotinimide adenine dinucleotide; penicillin; 1-piperidinyl ethanol; 1,4-diazbicyclo(2.2.2)octane; 1,4-diaminobutane; 1,5-diaminopentane; 1,6-diaminohexane; ethylenediamine; ethylenediamine tetraacetic acid; benzenesulfonamide; tetramethylsulfone; ethylamine; n-propylamine; n-butylamine; s-butylamine; t-butylamine; n-pentylamine; n-hexylamine; oxalic acid; hydrazine sulfate; glucose; methylacetamide; and phosphoroacetic acid.

The concentration of coreactant in the sample composition varies according to the specific coreactant chosen, and one of ordinary skill in the art is readily able to determine a suitable concentration. Typically, the coreactant concentration is chosen to be approximately 1000 times greater than the concentration of ECL label.

The ECL assay media may also comprise one or more ECL enhancers, which may increase ECL emission and may also serve as surfactants or wetting agents to prevent or reduce adsorption on the electrode and/or interior walls of the ECL apparatus. A number of ECL enhancers are well known in the art. See, for example, Shah et al., 1990. One group of ECL enhancers may be described as para-substituted benzenes wherein one substituent ($R_1$) is hydrogen or a $C_{1-20}$ alkyl group and the other (para) substituent ($R_2$) is a poly(alkoxy) alcohol of the formula —$[O—(CH_2)_n]_m$ OH where n is an integer from 1 to 20 and m is an integer from 0 to 70. One ECL enhancer, which is commercially available under the name Triton X-100®, has $R_1$ as —$C(CH_3)_2CH_2C(CH_3)_3$ and $R_2$ as —$(O—CH_2CH_2)_{9-10}OH$. Another ECL enhancer, which is commercially available under the name Triton X-401®, has $R_1$ as —$C_9H_{19}$ and $R_2$ as —$(O—CH_2CH_2)_{40}OH$. When utilized, the ECL enhancer is generally present in an amount which increases the ECL emission. Typically, the amount is from about 0.01 to about 5% (v/v), and often from about 0.1 to about 1% (v/v).

E. EXAMPLES

Several embodiments of the present invention are described in the following examples, which are offered by way of illustration and not by way of limitation.

Example 1

$Ru(bpy)_3^{+2}$/TPAH ECL Quenching by Phenol

An appropriate amount of tris(2,2'-bipyridyl)ruthenium (II) chloride hexahydrate (i.e., $Ru(bpy)_3Cl_2 6H_2O$, Aldrich® Chemical Co.) was dissolved in Elecsys® buffer solution (flash-ECL assay buffer number 1518-001; a phosphate based buffer with 0.18 M tri-n-propylamine (TPAH) and Thesit® as a wetting agent and ECL enhancer) and the solution diluted to yield a stock solution of 0.4 μM Ru$(bpy)_3^{2+}$ (as luminophore) and 0.18 M TPAH (as coreactant) at pH=6.8. Microliter amounts of 1 M phenol (i.e., $C_6H_5OH$, ultrapure, Clontech®) (as ECL quencher) dissolved in ethanol were added to 1 mL aliquots of stock solution to yield samples with phenol concentrations ranging from 2 to 15 mM.

ECL intensity was measured and recorded (in arbitrary units, e.g., counts) for each of the samples using a commercially available electrochemiluminescence analyzer, the Origen I Analyzer®, which integrates a photometer, a potentiostat, an electrochemical cell, and means for fluid and sample handling. The analyzer employs a flow injection system that permits rapid and reproducible determinations of sequential samples. The photometer is a red-sensitive photomultiplier tube positioned directly above the working electrode so that the light generated at or near the electrode is recorded and integrated during each measurement. Typically, an oxidative electrochemical sequence/potential was applied to the working electrode, and light intensity measured with a photomultiplier tube using standard Origen® parameters. Typically, the potential was ramped from 0 to 2800 mV at a sweep rate of 4800 mV/s (frequency=0.58 sec$^{-1}$). The electrode was cleaned prior to and after each run using a 0.176 M KOH buffered cleaning solution (Flash-ECL CS, from Boehringer Mannheim®, identification number 1518470). An EG&G PAR Model 263A® Potentiostat/Galvanostat was used for all electrochemical measurements.

The data are illustrated in FIG. 1. Note that the ECL signal for the sample having no phenol was greater than the detection capacity of the instrument, 10 million arbitrary units. Only 2 mM phenol resulted in the ECL being reduced to less than 7% of the ECL of the control sample. Only 5 mM phenol resulted in the ECL being reduced to less than about 0.01% of the ECL of the control sample.

This example demonstrates that micromolar concentrations of phenol effectively quench solution ECL of micromolar concentrations $Ru(bpy)_3^{2+}$ in the $Ru(bpy)_3^{2+}$/TPAH ECL reaction sequence. That is, upon electrochemical oxidation, the resulting excited state species, $Ru(bpy)_3^{2+*}$, is effectively quenched such that substantially less ECL intensity is observed as compared to the case where the quencher species is absent.

Example 2

$Ru(bpy)_3^{+2}/C_2O_8^{-2}$ ECL Quenching by Phenol

Figure 2:
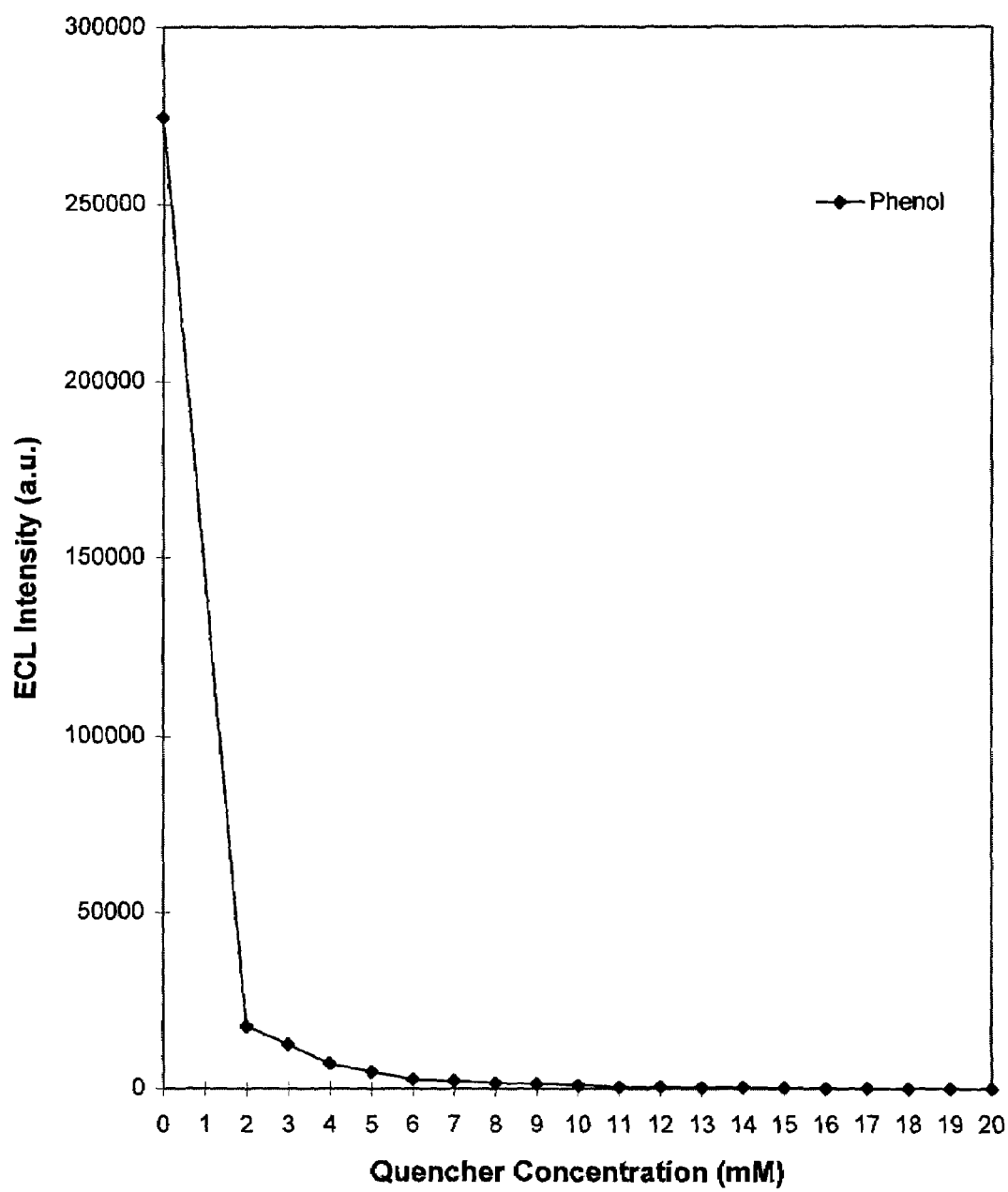
FIG. 2 is a graph depicting $Ru(bpy)_3^{+2}/C_2O_8^{-2}$ ECL intensity versus concentration of phenol (as a quenching agent), as described in Example 2 below.

Appropriate amounts of $Ru(bpy)_3Cl_2 6H_2O$ and $Na_2C_2O_8$ (Aldrich Chemical Company) were dissolved in phosphate buffered saline (i.e., "PBS"; 50 mM $Na_3PO_4$, 100 mM NaCl, pH 7.0, 0.2 µm filtered) and diluted to yield a stock solution of 0.4 µM $Ru(bpy)_3^{2+}$ (as luminophore) and 200 mM $C_2O_8^{-2}$ (as coreactant) at pH=7.0. Microliter amounts of 1 M phenol (as ECL quencher) dissolved in ethanol were added to 1 mL aliquots of stock solution to yield samples with phenol concentrations ranging from 2 to 20 mM. ECL intensity was measured and recorded (in arbitrary units) for each of the samples. The data are illustrated in FIG. 2. 2 mM phenol resulted in the ECL being reduced to less than 6% of the ECL of the control sample. 8 mM phenol resulted in the ECL being reduced to less than about 0.1% of the ECL of the control sample.

This example demonstrates that micromolar concentrations of phenol effectively quench ECL of sub-micromolar concentrations $Ru(bpy)_3^{2+}$ in the $Ru(bpy)_3^{2+}/C_2O_8^{-2}$ ECL reaction sequence. Although the ECL intensity of the $Ru(bpy)_3^{2+}/C_2O_8^{-2}$ system is intrinsically lower than that of the $Ru(bpy)_3^{2+}/TPAH$ system (by a factor of about 10-50), the use of phenol in the $C_2O_8^{-2}$ system did yield approximately 5% higher quenching efficiency.

Example 3

$Ru(bpy)_3^{+2}$ ECL Quenching by p-Hydroxybenzoic Acid and p-Aminobenzoic Acid

Figure 3:
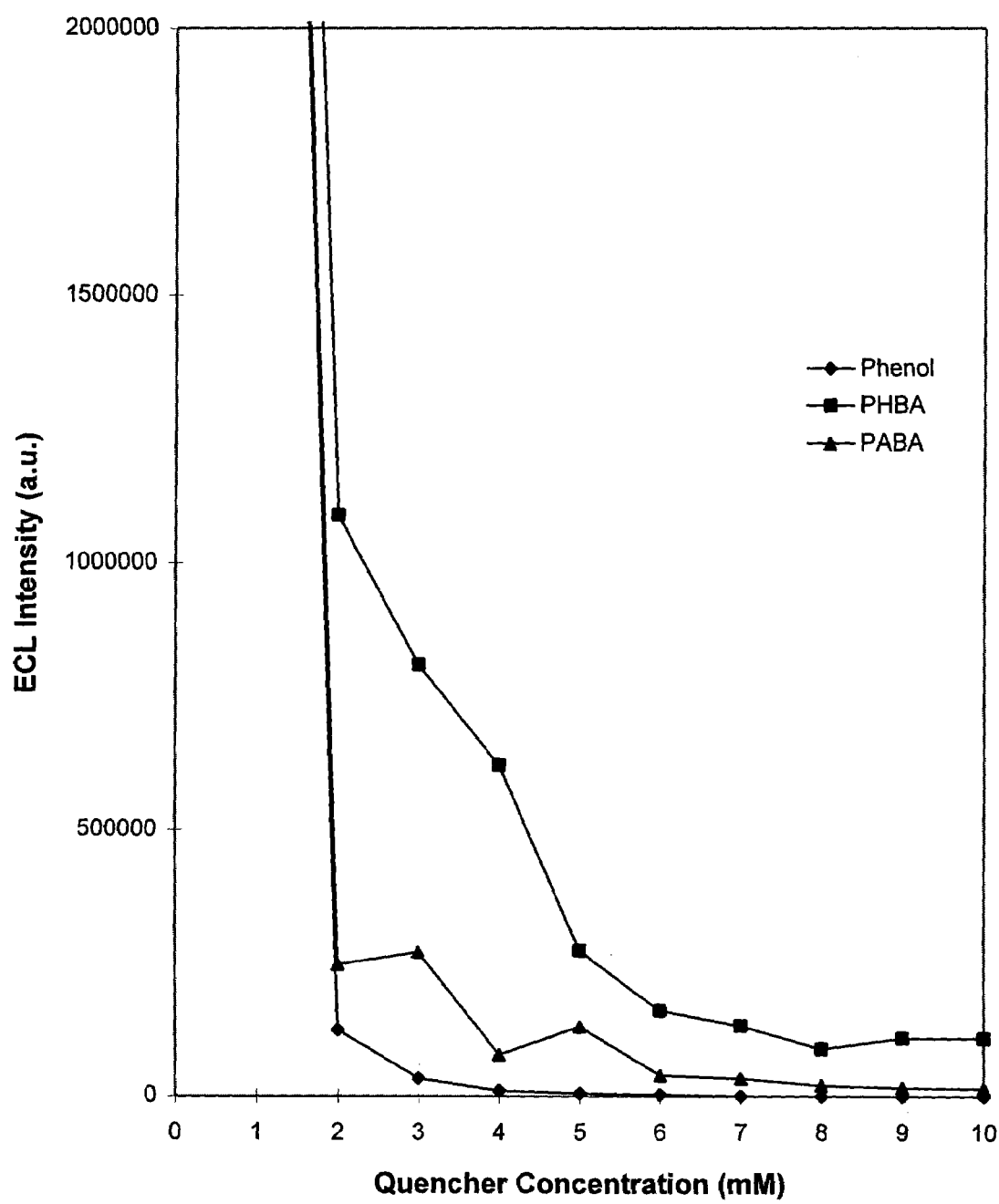
FIG. 3 is a graph depicting $Ru(bpy)_3^{+2}$/TPAH ECL intensity versus concentration of phenol, p-hydroxybenzoic acid (PHBA), and p-aminobenzoic acid (PABA) (as quenching agents), as described in Example 3 below.

An appropriate amount of $Ru(bpy)_3Cl_2.6H_2O$ was dissolved in Elecsys® buffer solution and diluted to yield a stock solution of 0.3 µM $Ru(bpy)_3^{2+}$ (as luminophore) and 0.18 M TPAH (as coreactant) at pH=6.8. Microliter amounts of 1 M p-hydroxybenzoic acid (i.e., $HOC_6H_4COOH$, PHBA, 99+% purity, Aldrich Chemical Company) or 1 M p-aminobenzoic acid (i.e., $H_2NC_6H_4COOH$, PABA, 99+% purity, Aldrich Chemical Company) (as ECL quencher) dissolved in ethanol were added to 1 mL aliquots of stock solution to yield samples with quenching agent concentrations ranging from 2 to 10 mM. For comparison, microliter amounts of 1 M phenol (as ECL quencher) dissolved in ethanol were added to 1 mL aliquots of stock solution to yield samples with phenol concentrations ranging from 2 to 10 mM. ECL intensity was measured and recorded (in arbitrary units) for each of the samples. The data are illustrated in FIG. 3.

This example demonstrates that, at comparable concentrations, phenol quenches the ECL of micromolar concentrations $Ru(bpy)_3^{2+}$ in the $Ru(bpy)_3^{2+}/TPAH$ ECL reaction sequence much more efficiently than either PHBA (by a factor of at least about 8) or PABA (by a factor of at least about 2). This example also demonstrates, via the known free radical scavengers PHBA and PABA, that interception of the TPA* intermediate prior to formation of the $Ru(bpy)_3^{2+*}$ excited state is less likely than direct quenching of the excited state.

Example 4

$Ru(bpy)_3^{+2}$ ECL Quenching by Phenol Derivatives

A number phenol derivatives, possessing one or more electron withdrawing and/or electron donating groups, were tested for their quenching efficiency in a manner analogous to that used in Example 3. Quenching agents (all >98% purity, from Aldrich Chemical Company) were dissolved to the appropriate concentration in ethanol, and appropriate aliquots were transferred to 1 mL aliquots of a $Ru(bpy)_3^{2+}/TPAH$ stock solution. Those phenol derivatives which were tested as quenching agents included: o-cresol (i.e., 2-methyl-phenol), m-cresol (i.e., 3-methyl-phenol), p-cresol (i.e., 4-methyl-phenol), p-fluorophenol, m-fluorophenol, o-fluorophenol, o-propylphenol, p-propylphenol, p-phenylphenol, o-trifluoromethylphenol, m-trifluoromethylphenol, p-trifluoromethylphenol, p-nitrophenol, p-nitrobenzoic acid, p-hydroxybenzoic acid, and 4,4'-biphenol.

Trends were observed in ECL quenching efficiency of the different phenol derivatives. Most notably, more efficient ECL quenching was observed when substituents were meta to the phenol hydroxyl group. For example, m-fluorophenol exhibited more efficient ECL quenching as compared to either o-fluorophenol or p-fluorophenol. Surprisingly, phenol was approximately a factor of 3 more efficient at ECL quenching than any of the phenol derivatives tested.

Example 5

The Effect of Phenol on $Ru(bpy)_3^{2+}$ Photoluminescence

An appropriate amount of $Ru(bpy)_3Cl_2 6H_2O$ was dissolved in Elecsys® buffer solution and diluted to yield a stock solution of 30 µM $Ru(bpy)_3^{2+}$ (as luminophore) and 0.18 M TPAH (as coreactant) at pH=6.8. Quantities of 0.2-0.3 M phenol dissolved in ethanol were added to 10 mL aliquots of stock solution to yield samples with phenol concentrations ranging from 0 to 0.3 M. The photoluminescence was measured for each of the samples (with no electrolysis) using a Perkin Elmer LS-50B fluorimeter with the voltage of the PMT biased at 850 V. Excitation was at 452 nm, the peak maximum of the lowest energy metal-to-ligand charge transfer (MLCT) absorption for the $Ru(bpy)_3^{2+}$ luminophore, with detection between 550 and 650 nm ($\lambda_{em}$=620 nm). The data showed that the photoluminescence increased steadily as the concentration of phenol increased. Note that this trend is opposite to the effect observed for increasing phenol concentration with ECL. Also, the data showed that the effect of phenol on fluorescence was much less dramatic than the effect on ECL.

Example 6

The Effect of Phenol on $Ru(bpy)_3^{2+}$ Photoluminescence: Bulk Electrolysis

An appropriate amount of $Ru(bpy)_3Cl_2 6H_2O$ and TPAH was dissolved in Elecsys® buffer solution and the solution diluted to yield a stock solution of 30 µM $Ru(bpy)_3^{2+}$ and 0.18 M TPAH at pH=6.8. To a 100 mL aliquot of stock solution was added 6 mL of 1 M phenol, yielding a phenol concentration of 60 mM. A baseline photoluminescence measurement was taken for this initial solution. Controlled potential coulometry (bulk electrolysis) was then performed for 3 hours with continuous stirring using a standard 3-electrode system available from BioAnalytical Systems® Inc. A reticulated vitreous carbon working electrode was biased to an oxidative potential of +1.3 V (versus a Ag/AgCl gel electrode used as reference) to effect electrolysis. A platinum wire counter electrode was separated from the working solution via a porous Vycor® frit, and immersed in an appropriate electrolyte solution. During the 3 hour bulk electrolysis, 1 mL samples were taken at ~30 minute intervals for photoluminescence testing ($\lambda_{exc}$=452 nm;$\lambda_{em}$=610 nm), as in Example 5. Approximately 50% of the photoluminescence signal was lost after 2 hr 45 min, indicating that a product of oxidation is directly responsible for photoluminescence quenching. Presumably this product of oxidation is also responsible for the observed ECL quenching.

Example 7

Catechol, Hydroquinone, and 1,4-Benzoquinone Quenching of $Ru(bpy)_3^{+2}$ ECL.

Figure 4:
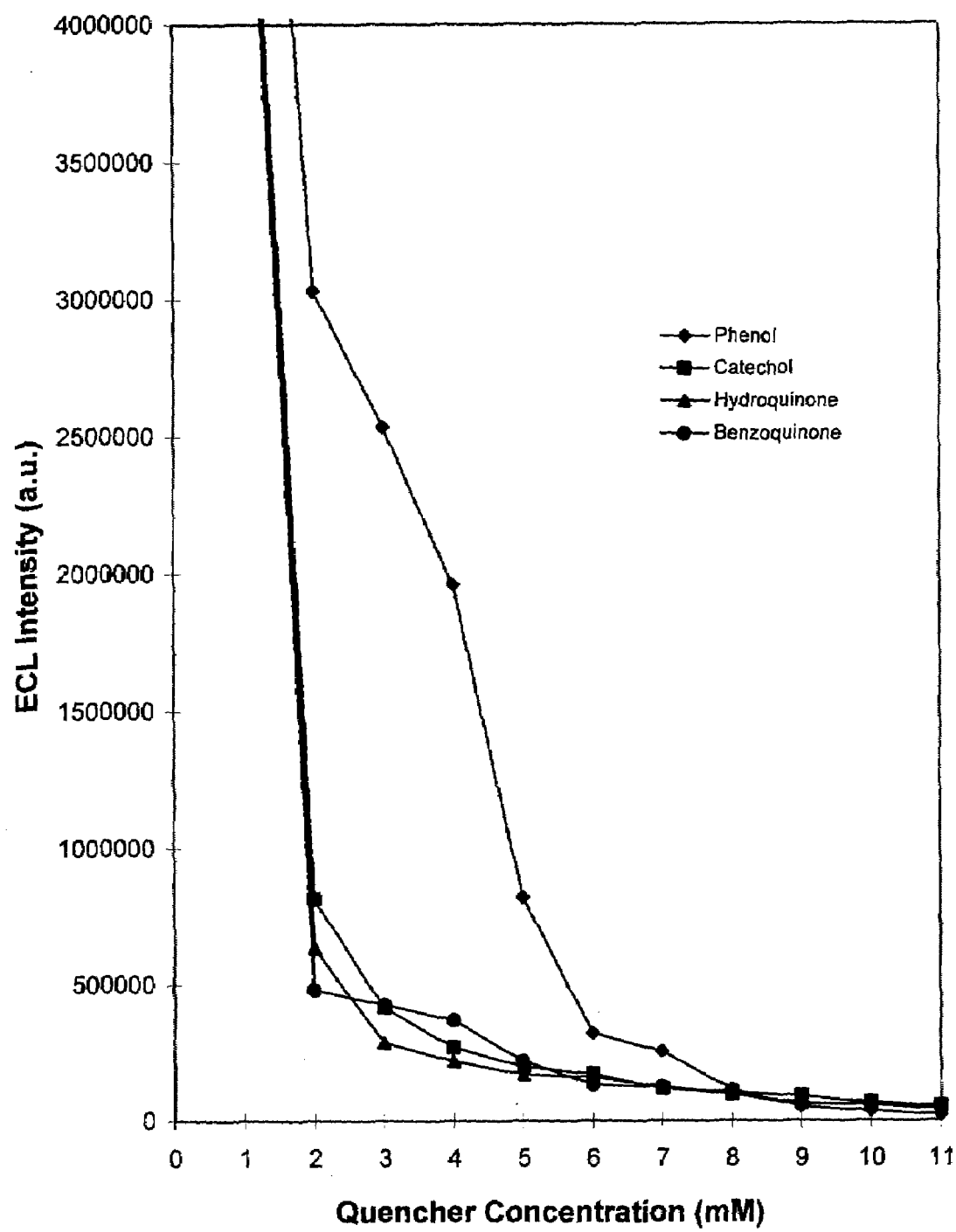
FIG. 4 is a graph depicting $Ru(bpy)_3^{+2}$/TPAH ECL intensity versus concentration of phenol, catechol, hydroquinone, and quinone (as quenching agents), as described in Example 7 below.

An appropriate amount of $Ru(bpy)_3Cl_26H_2O$ and TPAH was dissolved in Elecsys® buffer solution and the solution diluted to yield a stock solution of 0.3 µM $Ru(bpy)_3^{2+}$ (as luminophore) and 0.05 M TPAH (as coreactant) at pH=6.8. Microliter amounts of 1 M catechol (i.e., 1,2-dihydroxybenzene), hydroquinone (i.e., 1,4-dihydroxybenzene), or 1,4-benzoquinone (all from Aldrich Chemical Company) (as ECL quencher) dissolved in ethanol were added to 1 mL aliquots of stock solution to yield samples with quenching agent concentrations ranging from 2 to 11 mM. For comparison, microliter amounts of 1 M phenol (as ECL quencher) dissolved in ethanol were added to 1 mL aliquots of stock solution to yield samples with phenol concentrations ranging from 2 to 11 mM. ECL intensity was measured and recorded (in arbitrary units) for each of the samples. The data are illustrated in FIG. 4.

This example demonstrates that, at comparable concentrations, catechol, hydroquinone, and 1,4-benzoquinone (the presumed electro-oxidation products of phenol) quench the ECL of micromolar concentrations $Ru(bpy)_3^{2+}$ in the $Ru(bpy)_3^{2+}$/TPAH ECL reaction sequence more efficiently than phenol, with benzoquinone, the most efficient of the three derivatives, being approximately 6 times more efficient than phenol.

Example 8

$Ru(bpy)_3^{+2}$ECL Quenching by 1,4-Benzoquinone Derivatives

A number benzoquinone derivatives were tested for their quenching efficiency in a manner analogous to that used in Example 7. Quenching agents were dissolved to the appropriate concentration in ethanol, and appropriate aliquots were transferred to 1 mL aliquots of a $Ru(bpy)_3^{2+}$/TPAH stock solution. Those benzoquinone derivatives which were tested as quenching agents included: 2,3-dichloro-5,6-dicyano-1,4-benzoquinone (DDQ); 2,5-dibromo-1,4-benzoquinone (BRBQ); 1,2,3,4-tetrafluoro-5,8-dihydroxy-anthraquinone (TFDAQ); 2-methoxy-3-methyl-1,4-naphthoquinone (MMNQ); and anthraquinone-1,5-disulfonic acid (all >98% purity, from Aldrich Chemical Company).

Figure 5:
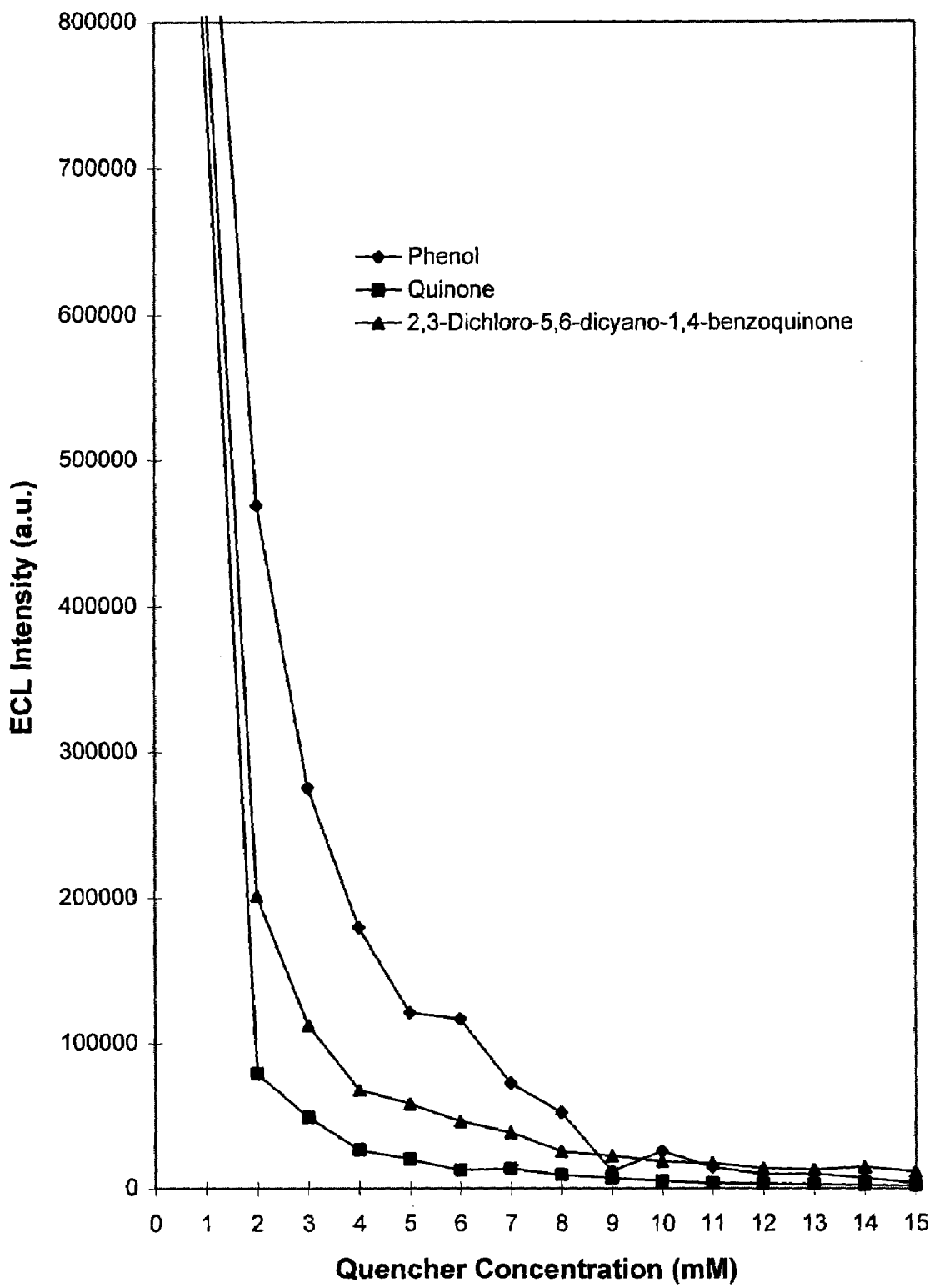
FIG. 5 is a graph depicting $Ru(bpy)_3^{+2}$/TPAH ECL intensity versus concentration of phenol, quinone, and 2,3-dichloro-5,6-dicyano-1,4-benzoquinone (DDQ) (as quenching agents), as described in Example 8 below.

ECL quenching data for phenol, BQ, and DDQ are shown in FIG. 5. DDQ, like many of the benzoquinone derivatives, was approximately a factor of 5 more efficient at ECL quenching than phenol. Benzoquinone was at least a factor of 3 more efficient at ECL quenching than any of the benzoquinone derivatives tested.

Example 9

The Effect of Hydroquinone, Catechol, and Benzoquinone on $Ru(bpy)_3^{2+}$ Photoluminescence An appropriate amount of $Ru(bpy)_3Cl_26H_2O$ was dissolved in Elecsys® buffer solution and diluted to yield a stock solution of 30 µM $Ru(bpy)_3^{2+}$ (as luminophore) and 0.18 M TPAH (as coreactant) at pH=6.8. To a 1.2 mL sample of stock solution were added 0.15 mL aliquots of 1 M hydroquinone (Aldrich Chemical Company) dissolved in ethanol. The photoluminescence was measured after each aliquot was added (with no electrolysis and prior to any bulk electrolysis) using the methods described above in Example 5. The data showed an approximately 10% increase in photoluminescence upon the addition of 0.45 mL of the 1 M hydroquinone solution. Note that this trend is opposite to the effect observed for increasing hydroquinone concentration with ECL.

A similar experiment was performed using 1 M catechol (Aldrich Chemical Company) instead of hydroquinone. Surprisingly, the incremental increase of catechol resulted in a decrease in photoluminescence, and approximately 70% of the photoluminescence signal was lost upon addition of 1.2 mL of 1 M catechol.

Another similar experiment was performed using 0.333 M benzoquinone (Aldrich Chemical Company) instead of hydroquinone. Again, the incremental increase of benzoquinone resulted in a decrease in photoluminescence, and approximately 100% of the photoluminescence signal was lost upon addition of 0.3 mL of 0.333 M benzoquinone. These results clearly demonstrate the efficiency of benzoquinone as a photoluminescence quencher.

Example 10

The Effect of Hydroquinone, Catechol, and Benzoquinone on $Ru(bpy)_3^{2+}$ Photoluminescence: Bulk Electrolysis An appropriate amount of $Ru(bpy)_3Cl_26H_2O$ and TPAH was dissolved in Elecsys® buffer solution and the solution diluted to yield a stock solution of 30 µM $Ru(bpy)_3^{2+}$ (as luminophore) and 0.05 M TPAH (as coreactant) at pH=6.8. To a 100 mL aliquot of stock solution was added 6 mL of 1 M hydroquinone (Aldrich Chemical Company), yielding a phenol concentration of 60 mM. Controlled potential coulometry (bulk electrolysis) was performed as described above in Example 6. After 45 minutes, the solution turned a reddish-brown color, indicative of the formation of benzoquinone or some derivative. Also, complete quenching of the photoluminescence was observed within 45 minutes. These data are similar to those observed for phenol, where a substance that enhances $Ru(bpy)_3^{2+}$ luminescence is electrochemically oxidized to form a product that efficiently quenches luminescence.

A similar experiment was performed using 6 mL of 1 M catechol instead of hydroquinone. A complete loss of luminescence was observed within 30 minutes with the concomitant formation of a reddish-brown solution. Although catechol does itself quench photoluminescence at these concentrations (see Example X), the electro-oxidation product of catechol is much more efficient at photoluminescence quenching.

Another similar experiment was performed using 1 mL of 0.333 M benzoquinone instead of hydroquinone. Little or no enhanced photoluminescence quenching was observed upon bulk electro-oxidation. This result is consistent with the conclusion that benzoquinone is responsible for the observed quenching. In fact, a slight increase in photoluminescence intensity was observed, indicating that upon prolonged oxidation, benzoquinone begins to decompose to form non-quenching products.

Example 11

$Ru(bpy)_3^{+2}$/TPAH ECL Quenching by Phenol: Electric Potential Studies

An appropriate amount of $Ru(bpy)_3Cl_26H_2O$ and TPAH was dissolved in Elecsys® buffer solution and the solution diluted to yield a stock solution of 0.3 µM $Ru(bpy)_3^{2+}$ (as luminophore) and 0.05 M TPAH (as coreactant) at pH=6.8. Microliter amounts of 1 M phenol (as ECL quencher) dissolved in ethanol were added 1 mL aliquots of stock solution to yield samples with phenol concentrations ranging from 2 to 6 mM. ECL intensity was measured and recorded (in arbitrary units) for each of the samples using the methods described above, but with potentials of 600, 1000, and 2800 mV in order to assess the degree of ECL quenching and the potentials at which full ECL quenching occurred.

The oxidation of $Ru(bpy)_3^{2+}$ to $Ru(bpy)_3^{3+}$ is known to proceed at +1.3 V versus Ag/AgCl. The oxidation of phenol to products occurs at about +1.0 V versus Ag/AgCl. As expected, little ECL was observed at potentials of less than +1.3 V versus Ag/AgCl, since at lower potentials the $Ru(bpy)_3^{2+}$ is not being oxidized. As expected, at higher phenol concentrations and at higher potentials, greater quenching was observed, supporting the conclusion that oxidation of both phenol and $Ru(bpy)_3^{2+}$ are needed for efficient ECL quenching.

Comparative Example 1

$Ru(bpy)_3^{+2}$ ECL Quenching by Methylviologen Carboxylate

Figure 6:
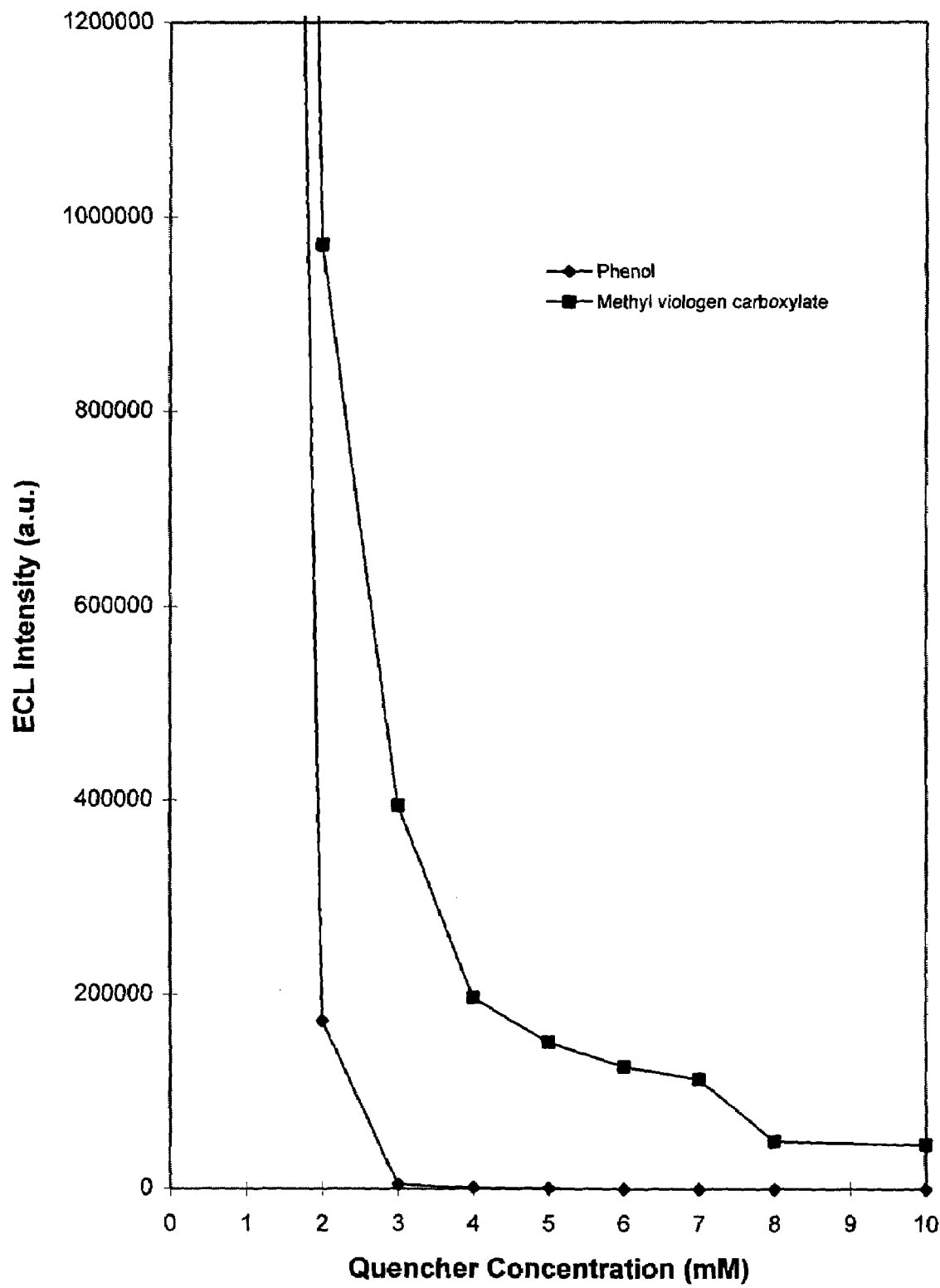
FIG. 6 is a graph depicting $Ru(bpy)_3^{+2}$/TPAH ECL intensity versus concentration of phenol (as a quenching agent) and methyl viologen carboxylate (for comparison), as described in Comparative Example 1 below.

An appropriate amount of $Ru(bpy)_3Cl_2 6H_2O$ was dissolved in Elecsys® buffer solution and diluted to yield a stock solution of 0.3 µM $Ru(bpy)_3^{2+}$ (as luminophore) at pH=6.8. Microliter amounts of aqueous 10 mM methylviologen carboxylate ($MV^{+2}$, 1,1'-dimethyl-4,4'-bipyridinium carboxylate dichloride) (as ECL quencher) were added to 1 mL aliquots of stock solution to yield samples with $MV^{+2}$ concentrations ranging from 2 to 10 mM. For comparison, microliter amounts of 1 M phenol (as ECL quencher) dissolved in ethanol were added to 1 mL aliquots of stock solution to yield samples with phenol concentrations ranging from 2 to 6 mM. ECL was measured for each of the samples, and the ECL intensity (in arbitrary units) recorded. The data are illustrated in FIG. 6.

This example demonstrates that, at comparable concentrations, phenol quenches the ECL of micromolar concentrations $Ru(bpy)_3^{2+}$ in the $Ru(bpy)_3^{2+}$/TPAH ECL reaction sequence approximately 10 times more efficiently than methylviologen carboxylate, the "gold standard" of $Ru(bpy)_3^{2+}$ ECL quenching.

Example 12

$Ru(bpy)_3^{+2}$/TPAH ECL Quenching by Phenol: Luminophore Immobilized (via Magnetic Particles) and Quenching Agent in Solution This example illustrates the quenching of an immobilized labeled complex, in this case, an oligonucleotide which was been labeled with the luminophore $Ru(bpy)_3^{+2}$ and subsequently attached to paramagnetic particles, by a quenching agent, in this case phenol, which is present in solution.

A test oligonucleotide consisting of 20 nucleotide residues was prepared using standard solid phase methods with a Perkin Elmer ABI 394 Synthesizer® using beta-cyanoethyl phosphoramidite chemistry. By using a commercially available (from Glen Research) derivatized controlled pore glass support, illustrated below, which has both a biotin-TEG group and a DMT protected hydroxyl group (i.e., —ODMT), the resulting oligonucleotide possesses, at the 3'-terminus, a tethered biotin group.

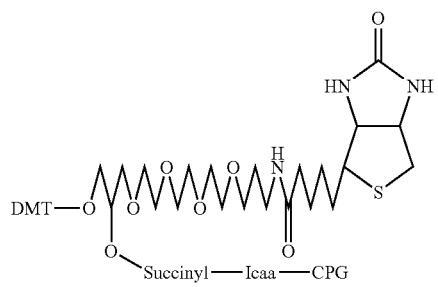

The oligonucleotide was synthesized using standard methods. Once the 20-mer oligonucleotide had been synthesized (having a DMT protected 5'-hydroxyl group), a final reaction sequence was performed using the Synthesizer but employing, instead of a nucleotide monomer reagent, a phosphoramidite derivative of a $Ru(bpy)_3^{+2}$, shown below.

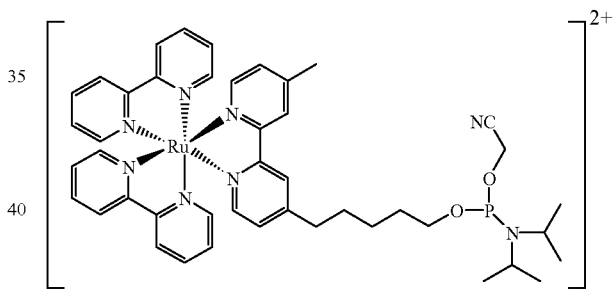

In this way, the 20-mer oligonucleotide (shown below) was obtained which possessed, at the 3'-end, a tethered biotin group and, at the 5'-end, a tethered $Ru(bpy)_3^{+2}$ moiety.

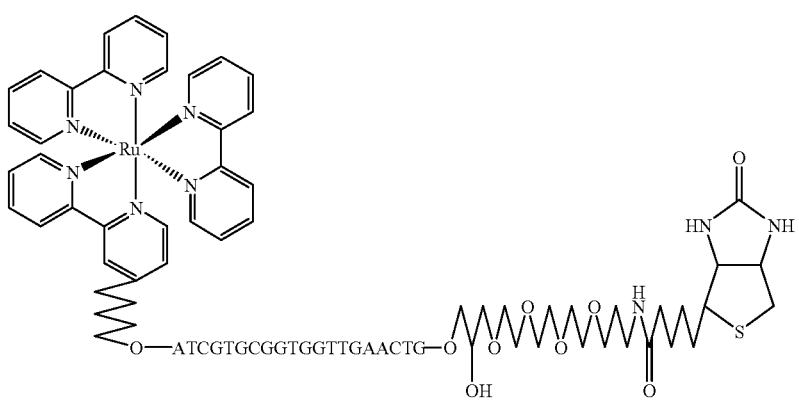

This derivatized oligonacleotide (SEQ ID NO:1) may be denoted as shown below (SEQ ID NO:2), wherein R denotes the Ru(bpy)$_3^{+2}$-containing group and B denotes the biotin-containing group.

```
5' - R -AT CGT GCG GTG GTT GAA CTG - B - 3'
```

Superparamagnetic particles (from Dynal Corp., Lake Success, N.Y.) comprising a magnetite (Fe$_3$O$_4$) core and a polystyrene outer coating, and having a size of about 2.8 μm, were coated with poly-streptavidin (a protein prepared from the culture supernatant of *Streptomyces avidinii* which has four high affinity binding sites for biotin). A solution of the labeled oligonucleotide was added to a suspension of the streptavidin-coated magnetic beads to yield labeled magnetic beads having bound labeled oligonucleotide.

Since phenol was to be added to some samples, a buffer solution was prepared based on Elecsys® buffer solution and formulated to have 27.19 g/L potassium phosphate monobasic (KH$_2$PO$_4$); 0.2 g/L Triton X-100 (t-octylphenoxy-polyethoxyethanol); and 0.05 M TPAH. The pH of the buffer solution was adjusted to 7.0 with 4M aqueous NaOH. For those cases where phenol was to be added to the buffer solution, 1.2 μL of 1 M phenol dissolved in ethanol was added to give 1 mM phenol and the pH again adjusted to 7.0 with 4 M aqueous NaOH.

A 3 μL aliquot of a suspension of labeled magnetic beads (546 pmol Ru(bpy)$_3^{+2}$ label) was added to 1 mL of buffer solution to yield a working bead solution. This working bead solution was placed in the ECL cell and the labeled magnetic particles immobilized onto the surface of the working electrode. Buffer solution containing coreactant (and, in some cases, phenol) was swept into the cell, and an appropriate potential is applied to generate signal. ECL was measured and recorded (in arbitrary units) for five control cases (using buffer without phenol) and ten quenching cases (using buffer with added phenol). In the control cases, ECL signals of about 75,000 arbitrary units were observed from the labeled beads in the absence of phenol. Virtually no ECL signal was observed for the labeled beads in the presence of phenol.

This example clearly demonstrates that in a magnetic bead format where the ECL luminophore is immobilized (in this case, attached to an oligonucleotide, and the oligonucleotide attached to a magnetic bead), quenching of the ECL luminophore still occurs.

Example 13

Ru(bpy)$_3^{+2}$/TPAH ECL Quenching by a Benzoquinone: Both Luminophore and Quenching Agent Immobilized (via Magnetic Particles)

This example illustrates the quenching of an immobilized labeled complex, in this case, an oligonucleotide which was been labeled with the luminophore Ru(bpy)$_3^{+2}$ and attached to paramagnetic particles, by a quenching agent, in this case a benzoquinone, which has also been attached to the oligonucleotide.

Three oligonucleotides consisting of 21 nucleotide residues were prepared using standard solid phase methods with a Perkin Elmer ABI 394 Synthesizer® using beta-cyanoethyl phosphoramidite chemistry, in a manner analogous to that described in Example 12. The three resulting derivatized oligonucleotides are illustrated below (SEQ ID NOS:3-5), where R denotes the Ru(bpy)$_3^{+2}$-containing group and B denotes the biotin-containing group.

```
5'- R - CAG TTC CAA CCA ACC GCA CGT - B -3'        (13-1-R)
5'- R - CAG TTC CAA CCA ACC GCA CGT - B -3'        (13-2-R)
5'- R - CAG TTC CAA CCA ACC GCA CGT LLLLL - B -3'  (13-3-R)
```

In the above formulae, T denotes "amine modified C$_6$-dT," a commercially available (from Glen Research) modified thymine nucleotide residue, illustrated below, which was introduced during oligonucleotide synthesis.

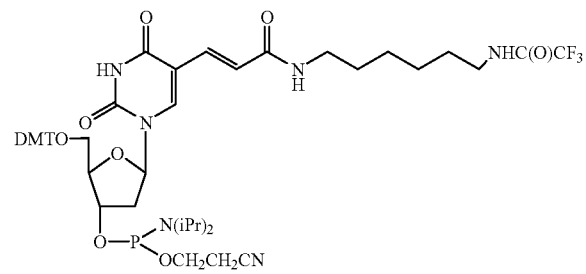

Also in the above formulae, L denotes "Label On," a commercially available (from Glen Research) reagent, illustrated below, which permits that attachment of common labels and which was introduced during oligonucleotide synthesis.

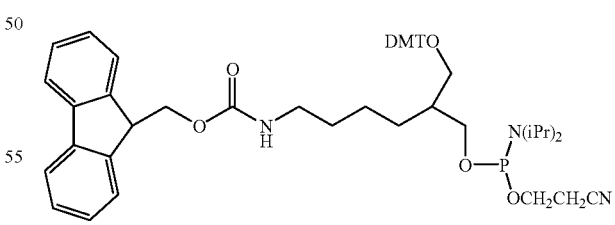

The above three derivatized oligonucleotides (each having a Ru(bpy)$_3^{+2}$ group) were employed as controls. Three test oligonucleotides, shown below (SEQ ID NOS:6-8), were prepared by attaching a benzoquinone moiety was at the position marked T and at each position marked L.

```
(13-1-RQ)
    5' - R - CAG T(Q)TC CAA CCA ACC GCA CGT - B - 3'

(13-2-RQ)
    5' - R - CAG TTC CAA CCA ACC GCA CGT(Q) - B - 3'

(13-3-RQ₅)
    5' - R - CAG TTC CAA CCA ACC GCA CGT L(Q)L(Q)L(Q)L(Q)L(Q) - B - 3'
```

For T, the protected amine group (i.e., —NHC(=O)CF$_3$) was first deprotected, and the free amine group subsequently reacted with the N-succinimidyl ester of a benzoquinone derivative, shown below. For L, the protected amine group (i e., —NHFMOC) was first deprotected, and the free amine was subsequently reacted with the same N-succinimidyl ester of the benzoquinone derivative.

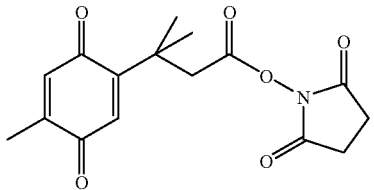

The three test oligonucleotides (and their standards) were quantified by UV-VIS absorption spectroscopy, using the absorbance of the Ru(bpy)$_3^{2+}$ moiety at 456 nm ($\epsilon$=13000 M$^{-1}$ cm$^{-1}$) so that equivalent amounts of each test oligonucleotide could be used for ECL analysis. In a manner analogous to that in Example 12, suitable amounts of each test oligonucleotide were added to suspensions of the streptavidin-coated magnetic beads to yield labeled magnetic beads having bound labeled oligonucleotide such that ⅓ saturation of streptavidin sites was achieved (576 pmol Biotin/DNA labeled probes).

Each labeled magnetic bead suspension was examined. A 3 μL aliquot of the labeled magnetic bead suspension was placed in 1 mL of Elecsys® buffer solution to yield a working bead solution. This working bead solution was placed in the ECL cell of the Origen analyzer and the labeled magnetic particles immobilized onto the surface of the working electrode. Elecsys® buffer solution containing coreactant was swept into the cell, and an appropriate potential was applied to generate signal. ECL was measured and recorded (in arbitrary units) for five replicates for each of the four test oligonucleotides.

For test oligonucleotide 13-1-RQ, in which the Ru (bpy)$_3^{2+}$ luminophore is separated from the quenching benzoquinone group by 4 nucleotide residues, the observed ECL intensity was approximately 53% less than that observed for the control oligonucleotide 13-1-R which has no quenching moiety.

For test oligonucleotide 13-2-RQ, in which the Ru (bpy)$_3^{2+}$ luminophore is separated from the quenching benzoquinone group by 21 nucleotide residues, the observed ECL intensity was approximately 49% less than that observed for the control oligonucleotide 13-2-R which has no quenching moiety.

For test oligonucleotide 13-3-RQ$_5$, in which the Ru (bpy)$_3^{2+}$ luminophore is separated from the (five) quenching benzoquinone groups by 21 nucleotide residues, the observed ECL intensity was approximately 20% less than that observed for the control oligonucleotide 13-3-R which has no quenching moiety.

This example clearly demonstrates that in a magnetic bead format where both the ECL luminophore and the quenching moiety are immobilized (in this case, both are attached to an oligonucleotide, and the oligonucleotide attached to a magnetic bead), quenching of the ECL luminophore still occurs.

Example 14

Ru(bpy)$_3^{+2}$/TPAH ECL Quenching by a Benzoquinone: Restriction Enzyme Methods This example illustrates the use of restriction enzymes coupled with bead capture and subsequent ECL detection. In this case, oligonucleotide hybridization probes are labeled with Ru(bpy)$_3^{2+}$ and biotin at the 3'-terminus and a quenching moiety at the 5'-terminus. Two pairs of oligonucleotides (SEQ ID NOS:9-12) having tethered biotin groups at the 3'-terminus are synthesized using standard solid phase methods as described in Example 12.

```
5' - NAC GCC ACT GGA TCC ACA GTT AGTc - B - 3'      (14-A-1)

5' - AAC GCC ACT GGA TCC ACA FTT AGTc - B - 3'      (14-A-2)

5' - T TTG CGG TGA CCT AGG TGT CAA TCA Tc - B - 3'  (14-B-1)

5' -   TTG CGG TGA CCT AGG TGT CCA TCA Tc - B - 3'  (14-B-2)
```

Each pair pertains to a separate example and each member of a given pair comprises the same specific probe sequence which is complementary to a sequence in a DNA target to be detected. The second member of each pair, which will not be derivatized to have a quenching moiety, is used for comparison purposes to verify quenching; the second member provides an indication of the ECL emission in the absence of a quenching moiety. The underlined residues, CCT AGG, identify part of the BamHI enzyme restriction site, as discussed below.

In the above formulae, T is as defined above in Example 13 and N denotes "5'-amino modifier," a commercially available (from Glen Research) reagent, illustrated below (where MMT is 4-monomethoxytrityl) which was introduced during oligonucleotide synthesis.

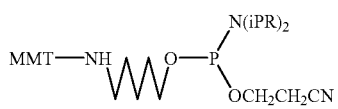

Also in the above formulae, Tc denotes "carboxy modified dT," a commercially available (from Glen Research) modified thymine nucleotide residue, illustrated below, which was introduced during oligonucleotide synthesis.

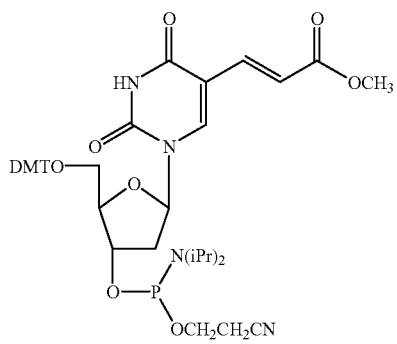

Following cleavage of the oligonucleotides from the solid phase support, a Ru(bpy)$_3^{2+}$ group is covalently attached at the 3'-terminus by reacting the following N-hydroxysuccinimidyl ester derivative with the carboxy group of Tc.

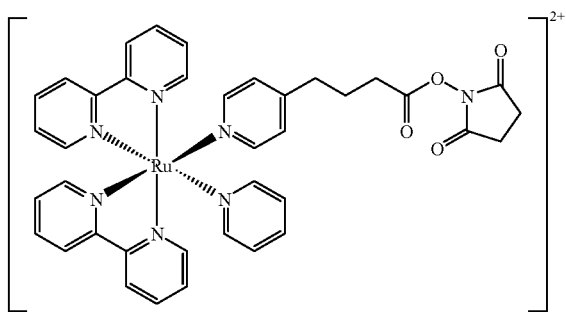

A quenching moiety is then covalently attached at the 5'-terminus of first member of each pair via the amino groups of N and T, using the activated benzoquinone derivative illustrated in Example 13. In this way, the following two pairs of derivatized oligonucleotide hybridization probes (SEQ ID NO:13-16) are obtained. The ECL emission of the first member of each pair is quenched by the presence of the quenching moiety, as illustrated by comparison with the ECL emission of the corresponding second member, which has no quenching moiety.

The first member of a pair of derivatized oligonucleotide hybridization probes (e.g., 14-A-1-BRQ or 14-B-1-BRQ) is then added to a sample containing single stranded DNA. The derivatized oligonucleotide probe will hybridize only with the complementary target sequence. The restriction enzyme BamHI is added. This enzyme recognizes only a specific double stranded DNA sequence, as shown below.

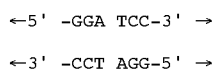

The restriction enzyme cleaves this sequence between the GG residues to yield two fragments, each with a 5'-overhang, as shown below.

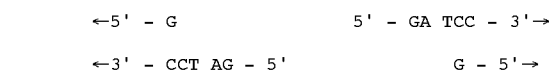

In this way, each target DNA sequence leads to a cleavage event, and the formation of a cleavage fragment which possesses an ECL label no longer in quenching contact with an ECL quenching moiety. These cleavage fragments also possess a biotin group (as well as an unquenched ECL label), which permit their capture (and optional separation) with the aid of streptavidin coated magnetic beads, as in Example 12. The ECL emission is then measured and correlated with the amount of target DNA in the original sample. Of course, bead capture may be performed prior to or after enzymatic cleavage.

Again, for comparison purposes, ECL emission is measured following hybridization and prior to enzymatic cleavage for the first and second members of a given pair. When the probe has hybridized with the target DNA, the ECL emission of the first member of each pair remains quenched by the presence of the quenching moiety, as illustrated by comparison with the ECL emission of the corresponding second member, which has no quenching moiety.

F. REFERENCES

The disclosures of the publications, patents, and published patent specifications referenced below are hereby incorporated by reference into the present disclosure to more fully describe the state of the art to which this invention pertains.

Abruna et al., 1985, "Electrochemiluminescence of Osmium Complexes. Spectral, Electrochemical, and Mechanistic Studies," *J. Electrochem. Soc., Electrochem. Sci. and Tech.*, Vol. 132, No. 4, pp. 842-849.

Bard et al., 1993, "Luminescent Metal Chelate Labels and Means for Detection," U.S. Pat. No. 5,221,605, issued Jun. 22, 1993.

Blackburn et al., 1991, "Electrochemiluminescence Detection for Development of Immunoassays and DNA Probe Assays for Clinical Diagnostics," *Clin. Chem.*, Vol. 37, No. 9, pp. 1534-1539.

```
5'- (Q)NAC GCC ACT GGA TCC ACA GTT AGTc(R) - B - 3'      (14-A-1-BRQ)

5'- AAC GCC ACT GGA TCC ACA FTT AGTc(R) - B - 3'         (14-A-2-BR)

5'- (Q)TTTG CGG TGA CCT AGG TGT CAA TCA Tc(R) - B - 3'   (14-B-1-BRQ)

5'- TTG CGG TGA CCT AGG TGT CCA TCA Tc(R) - B - 3'       (14-B-2-BR)
```

Chmura et al., 1994, "Assay of Antioxidants by the Quenching of the Anthracene-Sensitized Electrochemiluminescence," *J. Biolumin. Chemilumin.*, Vol. 9, pp. 1-6.

Coligan et al., 1991, eds., *Current Protocols in Immunology* (Published by Wiley & Co.).

Hall et al., 1991, "Method and Apparatus for Conducting Electrochemiluminescent Measurements," U.S. Pat. No. 5,068,088, issued Nov. 26, 1991.

Harrow & Lane, 1988, *Antibodies: A Laboratory Manual* (Cold Spring Harbor Laboratory).

Heid et al., 1996, "Real Time Quantitative PCR," *Genome Research*, Vol. 6, No. 10, October 1996, pp. 986-994.

Hill et al., 1988, "Electrochemiluminescence as a Detection Technique for Reversed-Phase High-Performance Liquid Chromatography. IV. Detection of Fluorescent Derivatives," *J. Chromatography*, Vol. 441, pp. 394-399.

Hoffmann, 1984, "Process for Making Human Antibody Producing B-Lymphocytes," U.S. Pat. No. 4,444,887, issued Apr. 24, 1984.

Kamin et al., 1992, "Method and Apparatus for Conducting Electrochemiluminescent Measurements," U.S. Pat. No. 5,147,806, issued Sep. 15, 1992.

Kenten et al., 1991, "Rapid Electrochemiluminscence Assays of Polymerase Chain Reaction Products," *Clin. Chem.*, Vol. 37, No. 9, pp. 1626-1632.

Kenten et al., 1992, "Rapid, Non-Separation Electrochemiluminescent DNA Hybridization Assays for PCR Products, Using 3'-Labeled Oligonucleotide Probes," *Mol. Cell. Probes*, Vol. 6, No. 6, pp. 495-503.

Knight et al., 1994, "Occurrence, Mechanisms and Analytical Applications of Electrogenerated Chemiluminscence," *Analyst*, Vol. 119, pp. 879-890.

Kricka, 1991, "Chemiluminescent and Bioluminscent Techniques," *Clin. Chem.*, Vol. 37, No. 9, pp. 1472-1481.

Kricka, 1992, ed., *Nonisotopic DNA Probe Techniques* (Academic Press, New York).

Leland et al., 1990, "Electrogenerated Chemiluminescence: An Oxidation-Reduction Type ECL Reaction Sequence Using Tripropyl Amine," *J. Electrochem. Soc.*, Vol. 137, No. 10, pp. 3127-3131.

Leland et al., 1992, "Methods and Apparatus for Improved Luminescence Assays," published international patent application no. WO 92/14139, published Aug. 20, 1992.

Maliwal et al., 1995, "Fluorescence Energy Transfer in One Dimension: Frequency-Domain Fluorescence Study of DNA-Fluorophore Complexes," *Biopolymers*, Vol. 35, pp. 245-255.

Masseyeff et al., 1993, eds., *Methods of Immunological Analysis* (Weinheim: VCH Verlags gesellschaft mbH).

Milstein et al., 1984, "Rat Myeloma Cell Lines," U.S. Pat. No. 4,472,500, issued Sep. 18, 1984.

Shah et al., 1990, "Enhanced Electrochemiluminescence," published international patent application no. WO 90/05302, published May 17, 1990.

Tyagi et al., 1996, "Molecular Beacons: Probes that Fluoresce upon Hybridization," *Nature Biotechnology*, Vol. 14, pp. 303-308, March 1996.

Ullman et al., 1976, "Fluorescent Quenching with Immunological Pairs in Immunoassays," U.S. Pat. No. 3,996,345, issued Dec. 7, 1976.

Ullman et al., 1981, "Fluorescence Quenching With Immunological Pairs in Immunoassays," U.S. Pat. No. 4,261,968.

Ullman, 1979, "Double Receptor Fluorescent Immunoassay," U.S. Pat. No. 4,161,515, issued Jul. 17, 1979.

Wands et al., 1985, "Process for Producing Antibodies to Hepatitis Virus and Cell Lines Therefor," U.S. Pat. No. 4,491,632, issued Jan. 1, 1985.

Weir et al., 1996, eds., *Handbook of Experimental Immunology*, 5th Edition (Blackwell Science).

Wild, 1994, ed., *The Immunoassay Handbook* (Stockton Press, N.Y.).

Wittwer et al., 1997, "Continuous Fluorescence Monitoring of Rapid Cycle DNA Amplification," *Biotechniques*, Vol. 22, pp. 133-138, January 1997.

Yoshida et al., 1980, "Antienzyme Homogeneous Competitive Binding Assay," U.S. Pat. No. 4,233,401, issued Nov. 11, 1980.

Yost, 1993, "Electrochemiluminescence (ECL)—A New Detection System for Immunoassays and DNA Probe Assays," in *Scientific Bavaria '92, 4th International Symposium, Progress in Laboratory Diagnostics*, eds. W. Holzel and S. Klose, published by Urban & Vogel, Munchen, pp. 82-90.

Zuk et al., 1980, "Label Modified Immunoassays," U.S. Pat. No. 4,208,479, issued Jun. 17, 1980.

Zuk et al., 1981, "Fluorescent Scavenger Particle Immunoassay," U.S. Pat. No. 4,256,834, issued Mar. 17, 1981.

The invention claimed is:

1. A method for qualitative or quantitative electrochemiluminescence detection of an oligonucleotide target analyte in a sample, the method comprising the steps of:
   (a) preparing an assay mixture comprising:
      (i) the sample,
      (ii) one or more assay reagents comprising a labeled complex comprising an electrochemiluminescent label selected from the group consisting of ruthenium bipyridine complexes and osmium bipyridine complexes attached to an oligonucleotide probe complementary to the analyte and hybridizing therewith, the label being capable of generating a detectable electrochemiluminescent emission, wherein the labeled complex is immobilized on a magnetic particle,
      (iii) an electrochemiluminescence quenching moiety selected from the group consisting of phenol and benzoquinone, and
      (iv) a coreactant,
   (b) bringing the assay mixture into contact with a working electrode,
   (c) applying a potential to the electrode, thereby enabling an electrochemiluminescence reaction to proceed,
   (d) separating unhybridized labeled complex from hybridized labeled complex,
   (e) measuring the electrochemiluminescent emission produced by the label hybridized to the analyte via the oligonucleotide probe, and
   (f) correlating the measured electrochemiluminescent emission with the presence or amount of the analyte in the sample.

2. A method for qualitative or quantitative electrochemiluminescence detection of an oligonucleotide target analyte in a sample, the method comprising the steps of:
   (a) preparing an assay mixture comprising:
      (i) the sample,
      (ii) one or more assay reagents comprising a labeled complex comprising an electrochemiluminescent label selected from the group consisting of ruthenium bipyridine complexes and osmium bipyridine complexes attached to an oligonucleotide probe, complementary to the analyte and hybridizing therewith, the label being capable of generating a detectable electrochemiluminescent emission, the labeled complex further comprising an electrochemiluminescence quenching moiety selected from the group consisting of phenol and benzoquinone, the quenching moiety attached to the probe, wherein the labeled complex is immobilized on a magnetic particle, and
      (iii) a coreactant,
   (b) bringing the assay mixture into contact with a working electrode,
   (c) applying a potential to the electrode, thereby enabling an electrochemiluminescence reaction to proceed,
   (d) separating unhybridized labeled complex from hybridized labeled complex,
   (e) measuring the electrochemiluminescent emission produced by the label hybridized to the analyte via the oligonucleotide probe, and
   (f) correlating the measured electrochemiluminescent emission with the presence or amount of the analyte in the sample.

3. An assay reagent kit for qualitative or quantitative electrochemiluminescence detection of an oligonucleotide target analyte in a sample, the assay reagent kit comprising, in one or more containers in packaged combination:
   (i) one or more assay reagents comprising a labeled complex comprising an electrochemiluminescent label selected from the group consisting of ruthenium bipyride complexes and osmium bipyridine complexes attached to an oligonucleotide probe capable of hybridizing with the analyte, the label being capable of generating a detectable electrochemiluminescent emission, wherein the labeled complex is immobilized on a magnetic particle,
   (ii) an electrochemiluminescence quenching moiety selected from the group consisting of phenol and benzoquinone, and
   (iii) a coreactant.

4. An assay reagent kit for qualitative or quantitative electrochemiluminescence detection of an oligonucleotide target analyte in a sample, the assay reagent kit comprising, in one or more containers in packaged combination:
   (i) one or more assay reagents comprising a labeled complex comprising an electrochemiluminescent label selected from the group consisting of ruthenium bipyridine complexes and osmium bipyridine complexes attached to an oligonucleotide probe, capable of hybridizing with the analyte, the label being capable of generating a detectable electrochemiluminescent emission, the labeled complex further comprising an electrochemiluminescence quenching moiety selected from the group consisting of phenol and benzoquinone, the quenching moiety attached to the probe, wherein the labeled complex is immobilized on a magnetic particle, and
   (ii) a coreactant.

5. A method for detecting an analyte in a samDle composition, comprising the steps of:
   (a) preparing an assay mixture comprising:
      (i) said sample composition;
      (ii) a first reagent comprising an ECL label having a chemical moiety that has electrochemiluminescent properties, which ECL label is capable of providing an observed ECL emission: and
      (iii) a second reagent having an ECL quenching moiety that, when in quenching contact with an ECL label, attenuates the observed ECL emission thereby providing a reduced ECL emission, said ECL quenching moiety comprising at least one benzene moiety;
   (b) bringing the assay mixture into contact with a working electrode;
   (c) applying a potential to the electrode, thereby enabling an electrochemiluminescence reaction to proceed; and
   (d) detecting a difference between the observed ECL emission and the reduced ECL emission, and thereby confirming the presence of said analyte in the sample solution,
   wherein the analyte comprises an oligonucleotide, and the ECL label and the ECL quenching moiety are present on separate oligonucleotide hybridization probes, which probes bind to the oligonucleotide in quenching contact.

6. A method for detecting an analyte in a sample composition, comprising the steps of:
   (a) preparing an assay mixture comprising:
      (i) said sample composition;
      (ii) a first reagent comprising an ECL label having a chemical moiety that has electrochemiluminescent properties, which ECL label is capable of providing an observed ECL emission; and
      (iii) a second reagent having an ECL quenching moiety that, when in quenching contact with an ECL label, attenuates the observed ECL emission thereby providing a reduced ECL emission, said ECL quenching moiety comprising at least one benzene moiety;

(b) bringing the assay mixture into contact with a working electrode;

(c) applying a potential to the electrode, thereby enabling an electrochemiluminescence reaction to proceed: and (d) detecting a difference between the observed ECL emission and the reduced ECL emission, and thereby confirming the presence of said analyte in the sample solution, wherein the analyte comprises an oligonucleotide, and the ECL label and ECL quenching moiety are present in quenching contact on a single oligonucleotide hybridization probe that binds to the oligonucleotide, and wherein said method further includes the presence of a DNA polymerase that is capable of degrading said hybridization probe when bound to said oligonucleotide so that the ECL label and ECL quenching moiety are no longer in quenching contact.

7. A method for detecting an analyte in a sample composition, comprising the steps of:

(a) preparing an assay mixture comprising:
 (i) said sample composition;
 (ii) a first reagent comprising an ECL label having a chemical moiety that has electrochemiluminescent properties, which ECL label is capable of providing an observed ECL emission; and
 (iii) a second reagent having an ECL quenching moiety that, when in quenching contact with an ECL label, attenuates the observed ECL emission thereby providing a reduced ECL emission, said ECL quenching moiety comprising at least one benzene moiety;

(b) bringing the assay mixture into contact with a working electrode;

(c) applying a potential to the electrode, thereby enabling an electrochemiluminescence reaction to proceed; and (d) detecting a difference between the observed ECL emission and the reduced ECL emission, and thereby confirming the presence of said analyte in the sample solution, wherein the analyte comprises an oligonucleotide, and the ECL label and ECL quenching moiety are present on a single oligonucleotide hybridization probe, which probe has self-hybridization sequences and is capable of self-hybridization in the absence of said oligonucleotide, and wherein self-hybridization brings the ECL label and FOL quenching moiety into quenching contact.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
atcgtgcggt ggttgaactg        20

<210> SEQ ID NO 2
<211> LENGTH: 20
<212> TYPE: DNA

```
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)
<223> OTHER INFORMATION: Ru(bpy),(subscript 3, superscript
      +2)-containing group is bound to the adenine
<220> FEATURE:
<221> NAME/KEY: modified_base
<222> LOCATION: (20)
<223> OTHER INFORMATION: Biotin-containing group is bound to guanine

<400> SEQUENCE: 2
atcgtgcggt ggttgaactg                                                  20

<210> SEQ ID NO 3
<211> LENGTH: 21
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)
<223> OTHER INFORMATION: Ru(bpy)[subscript 3, superscript
      +2]-containing group is bound to cytosine
<220> FEATURE:
<221> NAME/KEY: modified_base
<222> LOCATION: (21)
<223> OTHER INFORMATION: Biotin-containing group is bound to thymine
<220> FEATURE:
<221> NAME/KEY: modified_base
<222> LOCATION: (4)
<223> OTHER INFORMATION: n denotes "amine modified C(subscript 6)-dT" -
      modified thymine residue

<400> SEQUENCE: 3
cagntccaac caaccgcacg t                                                21

<210> SEQ ID NO 4
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)
<223> OTHER INFORMATION: Ru(bpy)[subscript 3, superscript
      +2]-containing group is bound to cytosine
<220> FEATURE:
<221> NAME/KEY: modified_base
<222> LOCATION: (21)
<223> OTHER INFORMATION: n denotes "amine modified C(subscript 6)-dT" -
      modified thymine residue
<220> FEATURE:
<221> NAME/KEY: modified_base
<222> LOCATION: (21)
<223> OTHER INFORMATION: Biotin-containing group is bound to the
      modified thymine residue at position 21

<400> SEQUENCE: 4
cagttccaac caaccgcacg n                                                21

<210> SEQ ID NO 5
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
```

```
<222> LOCATION: (1)
<223> OTHER INFORMATION: Ru(bpy)[subscript 3, superscript
      +2]-containing group is bound to cytosine
<220> FEATURE:
<221> NAME/KEY: modified_base
<222> LOCATION: 21
<223> OTHER INFORMATION: Thymine has 5 "L" groups bound to it (L="Label
      On" - a commercially available reagent)
<220> FEATURE:
<221> NAME/KEY: modified_base
<222> LOCATION: (21)
<223> OTHER INFORMATION: Biotin-containing group is attached to the last
      "L" group bound to Thymine

<400> SEQUENCE: 5
cagttccaac caaccgcacg t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)
<223> OTHER INFORMATION: Ru(bpy)[subscript 3, superscript
      +2]-containing group is bound to cytosine
<220> FEATURE:
<221> NAME/KEY: modified_base
<222> LOCATION: (4)
<223> OTHER INFORMATION: n denotes "amine modified C(subscript 6)-dT"-
      modified thymine residue; modified thymine has a benzoquinone
      moiety attached
<220> FEATURE:
<221> NAME/KEY: modified_base
<222> LOCATION: (22)
<223> OTHER INFORMATION: Biotin-containing group is bound to thymine

<400> SEQUENCE: 6
cagntccaac caaccgcacg t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)
<223> OTHER INFORMATION: Ru(bpy)[subscript 3, superscript
      +2]-containing group is bound to cytosine
<220> FEATURE:
<221> NAME/KEY: modified_base
<222> LOCATION: (21)
<223> OTHER INFORMATION: n denotes "amine modified C(subscript 6)-dT"-
      modified thymine residue;  modified thymine has benzoquinone
      moiety attached
<220> FEATURE:
<221> NAME/KEY: modified_base
<222> LOCATION: (21)
<223> OTHER INFORMATION: Biotin-containing group is bound to the
      modified thymine

<400> SEQUENCE: 7
cagttccaac caaccgcacg n                                              21

<210> SEQ ID NO 8
<211> LENGTH: 21
<212> TYPE: DNA
<213> ORGANISM: Artificial Sequence
```

```
<220> FEATURE:
<223> OTHER INFORMATION: Synthetic construct
<220> FEATURE:
<221> NAME/KEY: modified_base
<222> LOCATION: (1)
<223> OTHER INFORMATION: Ru(bpy)[subscript 3, superscript
      +2]-containing group is bound to cytosine
<220> FEATURE:
<221> NAME/KEY: modified_base
<222> LOCATION: 21
<223> OTHER INFORMATION: Thymine has 5 "L" groups bound to it (L="Label
      On" - a commercially available reagent; each "L" group has a
      benzoquinone moiety attached; last benzoquinone moiety
      has biotin-containing group attached

<400> SEQUENCE: 8
cagttccaac caaccgcacg t                                             21

<210> SEQ ID NO 9
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)
<223> OTHER INFORMATION: "5'-amino modifier" is bound to adenine
<220> FEATURE:
<221> NAME/KEY: modified_base
<222> LOCATION: (23)
<223> OTHER INFORMATION: n denotes "carboxyl modified dT"-modified
      thymine residue
<220> FEATURE:
<221> NAME/KEY: modified_base
<222> LOCATION: (23)
<223> OTHER INFORMATION: Biotin-containing group is bound to the
      modified thymine

<400> SEQUENCE: 9
acgccactgg atccacagtt agn                                           23

<210> SEQ ID NO 10
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (24)
<223> OTHER INFORMATION: n denotes "carboxyl modified dT"-modified
      thymine residue
<220> FEATURE:
<221> NAME/KEY: modified_base
<222> LOCATION: (24)
<223> OTHER INFORMATION: Biotin-containing group is bound to the
      modified thymine
<220> FEATURE:
<221> NAME/KEY: modified_base
<222> LOCATION: (19)
<223> OTHER INFORMATION: n is unknown.

<400> SEQUENCE: 10
aacgccactg gatccacant tagn                                          24

<210> SEQ ID NO 11
<211> LENGTH: 26
<212> TYPE: DNA
<213> ORGANISM: Artificial Sequence
<220> FEATURE:
<223> OTHER INFORMATION: Synthetic construct
```

```
<220> FEATURE:
<221> NAME/KEY: modified_base
<222> LOCATION: (1)
<223> OTHER INFORMATION: n denotes "amine modified C(subscript 6)-dT"-
      modified thymine residue
<220> FEATURE:
<221> NAME/KEY: modified_base
<222> LOCATION: (26)
<223> OTHER INFORMATION: n denotes "carboxyl modified dT"-modified
      thymine residue
<220> FEATURE:
<221> NAME/KEY: modified_base
<222> LOCATION: (26)
<223> OTHER INFORMATION: Biotin-containing group is bound to the
      modified thymine

<400> SEQUENCE: 11
nttgcggtga cctaggtgtc aatcan                                            26

<210> SEQ ID NO 12
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (25)
<223> OTHER INFORMATION: n denotes "carboxyl modified dT"-modified
      thymine residue
<220> FEATURE:
<221> NAME/KEY: modified_base
<222> LOCATION: (25)
<223> OTHER INFORMATION: Biotin-containing group is bound to the
      modified thymine
<220> FEATURE:

<400> SEQUENCE: 12
ttgcggtgac ctaggtgtcc atcan                                             25

<210> SEQ ID NO 13
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)
<223> OTHER INFORMATION: Adedine has bound to it a "5'-amino modifier"
      and a "quenching moiety"
<220> FEATURE:
<221> NAME/KEY: modified_base
<222> LOCATION: (23)
<223> OTHER INFORMATION: n denotes "carboxyl modified dT"-modified
      thymine residue
<220> FEATURE:
<221> NAME/KEY: modified_base
<222> LOCATION: (23)
<223> OTHER INFORMATION: Ru(bpy)[subscript 3, superscript
      +2]-containing group and biotin containing group is bound
      to the modified thymine

<400> SEQUENCE: 13
acgccactgg atccacagtt agn                                               23

<210> SEQ ID NO 14
<211> LENGTH: 24
<212> TYPE: DNA
<213> ORGANISM: Artificial Sequence
```

```
<220> FEATURE:
<223> OTHER INFORMATION: Synthetic construct
<220> FEATURE:
<221> NAME/KEY: modified_base
<222> LOCATION: (24)
<223> OTHER INFORMATION: n denotes "carboxyl modified dT"-modified
      thymine residue
<220> FEATURE:
<221> NAME/KEY: modified_base
<222> LOCATION: (24)
<223> OTHER INFORMATION: Ru(bpy)[subscript 3, superscript
      +2]-containing group and biotin containing group is bound
      to the modified thymine
<220> FEATURE:
<221> NAME/KEY: modified_base
<222> LOCATION: (19)
<223> OTHER INFORMATION: n is unknown.

<400> SEQUENCE: 14
aacgccactg gatccacant tagn                                        24

<210> SEQ ID NO 15
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)
<223> OTHER INFORMATION: n denotes "amine modified C, (subscript 6)-dT"-
      modified thymine with quenching moiety attached
<220> FEATURE:
<221> NAME/KEY: modified_base
<222> LOCATION: (26)
<223> OTHER INFORMATION: n denotes "carboxyl modified dT"-modified
      thymine residue
<220> FEATURE:
<221> NAME/KEY: modified_base
<222> LOCATION: (26)
<223> OTHER INFORMATION: Ru(bpy)[subscript 3, superscript
      +2]-containing group and biotin-containing group is bound
      to the modified thymine

<400> SEQUENCE: 15
nttgcggtga cctaggtgtc aatcan                                      26

<210> SEQ ID NO 16
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (25)
<223> OTHER INFORMATION: n denotes "carboxyl modified dT"-modified
      thymine residue
<220> FEATURE:
<221> NAME/KEY: modified_base
<222> LOCATION: (25)
<223> OTHER INFORMATION: Ru(bpy)[subscript 3, superscript +2]-containing
      group and biotin containing group is bound to the modified thymine

<400> SEQUENCE: 16
ttgcggtgac ctaggtgtcc atcan                                       25
```